(12) United States Patent
Molnar et al.

(10) Patent No.: US 8,109,633 B2
(45) Date of Patent: Feb. 7, 2012

(54) NONINVASIVE OCULAR MONITOR AND METHOD FOR MEASURING AND ANALYZING PHYSIOLOGICAL DATA

(76) Inventors: Lance Molnar, Morgantown, WV (US); James Trimmier, Morgantown, WV (US)

( * ) Notice: Subject to any disclaimer, the term of this patent is extended or adjusted under 35 U.S.C. 154(b) by 345 days.

(21) Appl. No.: 11/896,801

(22) Filed: Sep. 6, 2007

(65) Prior Publication Data

US 2008/0212026 A1  Sep. 4, 2008

Related U.S. Application Data

(60) Provisional application No. 60/842,372, filed on Sep. 6, 2006.

(51) Int. Cl.
*A61B 3/14* (2006.01)
*A61B 3/10* (2006.01)
*A61B 3/00* (2006.01)

(52) U.S. Cl. .......... 351/206; 351/221; 351/246

(58) Field of Classification Search ........... 351/200, 351/205–206, 221, 246; 514/912; 600/558, 600/561; 606/4
See application file for complete search history.

(56) References Cited

U.S. PATENT DOCUMENTS

| | | | |
|---|---|---|---|
| 4,993,825 A | 2/1991 | Abe et al. | |
| 5,125,730 A | 6/1992 | Taylor et al. | |
| 5,632,282 A * | 5/1997 | Hay et al. ............... | 600/558 |
| 5,778,893 A | 7/1998 | Potter | |
| 6,022,109 A | 2/2000 | Dal Santo | |
| 6,162,186 A | 12/2000 | Scinto et al. | |
| 6,305,804 B1 | 10/2001 | Rice et al. | |
| 6,547,394 B2 | 11/2001 | Doherty | |
| 6,544,193 B2 | 4/2002 | Abreu | |
| 6,387,618 B1 | 5/2002 | Kolanko et al. | |
| 6,477,394 B2 | 11/2002 | Rice et al. | |
| 6,565,210 B2 | 5/2003 | Kobayashi et al. | |
| 6,626,537 B1 | 9/2003 | Odom et al. | |
| 6,631,989 B2 | 10/2003 | Odom et al. | |
| 6,637,885 B2 | 10/2003 | Petrali | |
| 2004/0207811 A1* | 10/2004 | Elsner ............ | 351/205 |
| 2005/0057721 A1* | 3/2005 | Kolanko et al. ........ | 351/205 |
| 2007/0109499 A1* | 5/2007 | Yan et al. ............ | 351/221 |

OTHER PUBLICATIONS

International Search Report for PCT/US03/41220 dated Oct. 5, 2004.
International Search Report and Written Opinion for PCT/US07/077739, dated Aug. 20, 2008.

* cited by examiner

*Primary Examiner* — Ricky Mack
*Assistant Examiner* — Mahidere Sahle
(74) *Attorney, Agent, or Firm* — Patton Boggs LLP

(57) ABSTRACT

A non-invasive device and methods for acquiring and analyzing ocular images from a subject is presented. Aspects of the method comprise of the acquisition of ocular image(s) and subsequent evaluation, classification and/or interpretation of these image(s). The ocular image(s) are acquired using ocular scanning instruments or suitable substitutes. Evaluation, classification, and/or interpretation are most easily accomplished automatically through the use of one or more algorithms.

27 Claims, 17 Drawing Sheets

FUNDAS FLOW CHART

To FIG. 10B

NONINVASIVE OCULAR MONITOR AND METHOD FOR MEASURING AND ANALYZING PHYSIOLOGICAL DATA

CLAIM OF PRIORITY

This application claims priority to Provisional Application No. 60/842,372, filed Sep. 6, 2006, the contents of which are incorporated herein by reference in its entirety.

FIELD OF THE INVENTION

The present invention relates to non-invasive devices and method for measuring and analyzing ocular related characteristics in a patient. The measurement and analysis of the ocular related characteristics provide information about other physiological conditions in the patient by use of various methods and algorithms.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The sensitivity of the eye's reaction to a wide variety of chemicals/toxins and its role as a gauge for internal homeostasis (e.g., cardiovascular and neurophysiological imbalances) has been extensively researched and documented via many scientific disciplines. Such research has identified the eyes as a prominent indicator for various hazards and diseases. This indicator function of the eye is born from its tight interconnection with the cardiovascular, circulatory, lymphatic, ectodermal, and nervous systems of the body. Individual chemicals or compounds may create a unique "thumbprint" upon the eye based upon how they differentially affect the various physiological systems to which the eyes are interconnected. As a consequence, ocular characteristics may be employed for a variety of non-invasive diagnostic purposes based upon the pattern and quantitative extent of ocular biomarkers observed.

Since the development of the standardized grading systems in the 1930s to 1950s, great improvements have been made in the ability to image the eye. These include the development of nonmudriatic fundus cameras which permit fundus photography through undilated pupils, scanning laser opthalmoscopy which permits imaging the nerve fiber and optic blood flow, and fluoroscein angiography and idocyanine green angiography which permit imaging the retinal and choroidal vessels. Fluoroscein angiography also permits the imaging of the papillary vasculature. The development of these newer technologies has added to our knowledge of the changes in the eye with various diseases.

The indirect association of certain eye findings with certain disease states and exposure to hazards has been established for some time. One may legitimately ask why these associations are not exploited more vigorously in clinical medicine to evaluate and assist in classifying patients and then directing and monitoring their subsequent therapy. There are several reasons. First, those physicians who are primarily trained in the care of patients suffering from diseased states have little training in observing the ocular findings. Second, many times the ocular findings are not threatening to vision and, therefore, are of only moderate interest to physicians interested in treating eye disease. Finally, normal clinical evaluation of the ocular signs is difficult. This difficulty is due to both normal individual variability and because often some of the early changes seen in various diseases are also observed as the result of the normal aging process.

A need therefore exists for a non-invasive system and method for determining damage or abnormalities of the eye by obtaining ocular images.

SUMMARY OF THE INVENTION

In one embodiment, the present invention provides a non-invasive device for acquiring an ocular image, comprising: a) an optic assembly comprising one or more light emitting diodes (LEDs) and a lens; b) a Chip Charged Coupled Device (CCD); c) a linear activator to focus the optic assembly; and d) a toggle-switch activator. In an additional embodiment, the LEDs emit light at the wavelengths corresponding to white light and near infrared light. In another embodiment, the device is stationary. In yet another embodiment, the device is portable. In one embodiment, the device is handheld. In yet another embodiment, the device further comprises a light emitting diode (LED) display screen. In another embodiment, the LED display screen allows for user input.

The present invention further provides a non-invasive method of acquiring an ocular image from a subject, comprising acquiring the ocular image with the device of above. In a further aspect, the LEDs emit light at the wavelengths corresponding to visible light and near infrared light. In another aspect, the device is stationary. In yet another aspect, the device is portable. In still another aspect, the device is handheld. In a further aspect, the device comprises a light emitting diode display screen. In another aspect, the LED display screen allows for user input.

The present provides a non-invasive method of diagnosing a diseased state in a subject comprising: a) acquiring, processing and extracting one or more ocular characteristics according to the method of above; and b) comparing said ocular characteristics to a database of standard ocular characteristics obtained from a non-diseased state population; wherein differences between the subject's ocular characteristics and the database of standard ocular characteristics indicates an abnormality in the subject's ocular characteristics; and wherein any of steps a) through b) are performed under the control of an algorithm. In an additional embodiment, the diseased state is selected from the group consisting of exposure to organophosphate nerve agents, cyanide compounds, carbon monoxide and botulinum toxin. In another embodiment, the algorithm is as described herein.

In a further aspect, the present invention provides a non-invasive method of determining the progression of a diseased state in a subject comprising: a) acquiring, processing and extracting a first ocular characteristic according to the method of above; b) acquiring, processing and extracting a second ocular characteristic according to the method of above; and c) comparing the first ocular characteristic and the second ocular characteristic; wherein the first ocular characteristic and the second ocular characteristic are acquired, processed and extracted sequentially over time and wherein differences in the ocular characteristics indicate the relative change in diseased state status in said subject; and wherein any of steps a) through c) are performed under the control of an algorithm. In a further aspect, the diseased state is selected from the group consisting of exposure to organophosphate nerve agents, cyanide compounds, carbon monoxide and botulinum toxin. In another aspect, the algorithm is the algorithm is as described herein.

In a further aspect, the present invention further provides a non-invasive method for diagnosing a diseased state in a subject comprising: a) acquiring one or more ocular images with the device of above; b) processing said ocular images; c) extracting one or more ocular characteristics from said ocular images; and d) classifying said ocular characteristics; wherein any of steps a) through d) are performed under the control of an algorithm. In another embodiment, the diseased state is selected from the group consisting of exposure to organophosphate nerve agents, cyanide compounds, carbon monoxide and botulinum toxin. In yet another embodiment, the algorithm is described herein.

In another aspect, the present invention provides a non-invasive method of diagnosing a diseased state in a subject comprising: a) acquiring, processing and extracting one or more ocular characteristics according to the method of above; and b) comparing said ocular characteristics to a database of standard ocular characteristics obtained from a non-diseased state population; wherein differences between the subject's ocular characteristics and the database of standard ocular characteristics indicates an abnormality in the subject's ocular characteristics; and wherein any of steps a) through d) are performed under the control of an algorithm. In a further aspect, the diseased state is selected from the group consisting of exposure to organophosphate nerve agents, cyanide compounds, carbon monoxide and botulinum toxin. In yet another aspect, the algorithm is the algorithm is as described herein.

DETAILED DESCRIPTION OF THE INVENTION

Figure 1:
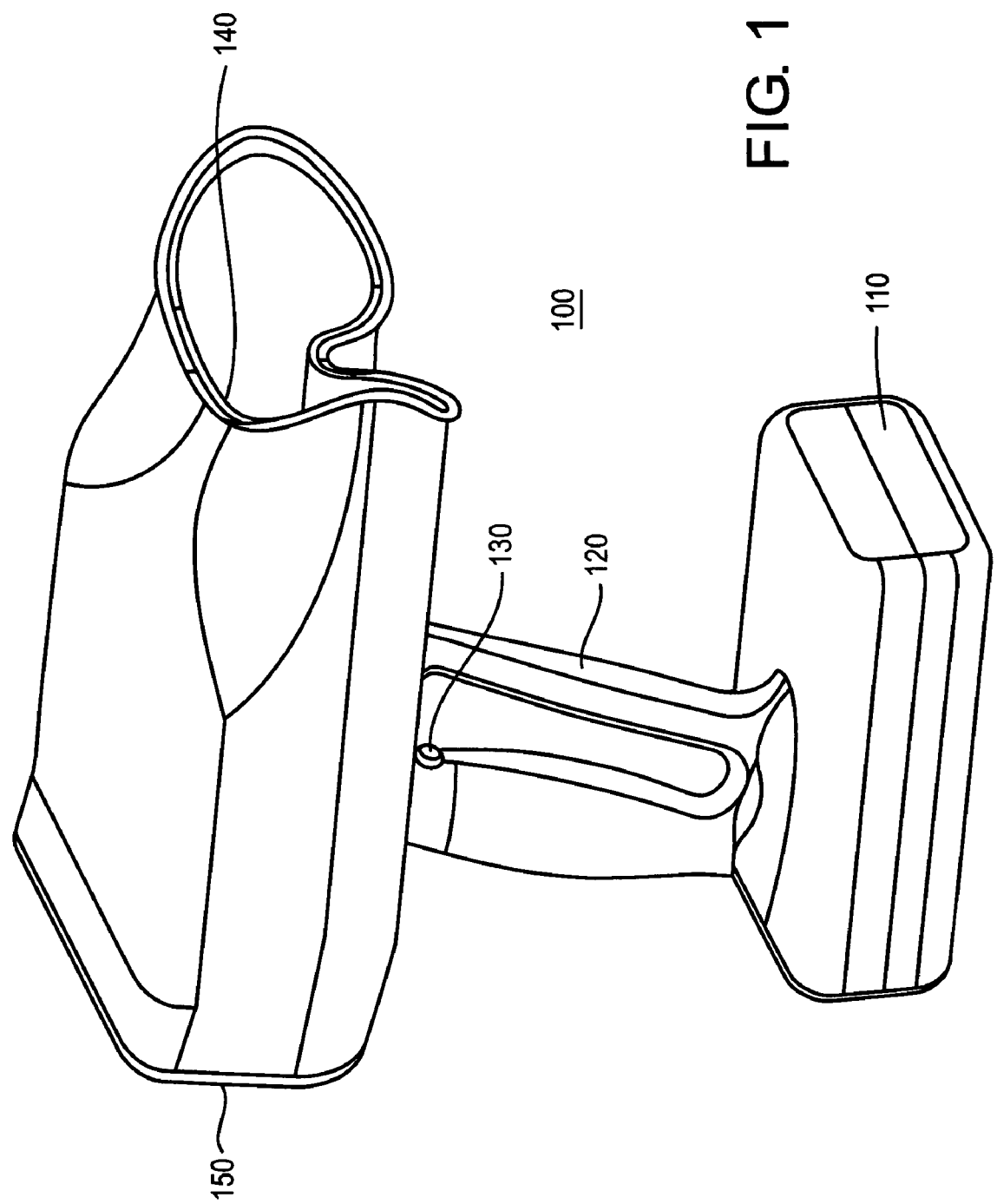
FIG. 1 is a schematic diagram illustrating an embodiment of the device of the invention.

Embodiments of the present invention are described in detail in the following.

As used herein, the term "subject" refers to human beings and other members of the animal kingdom unless in a specific usage and express indication to the contrary is provided.

An "ocular characteristic" is a measurable physical attribute determined via the observation of external or internal features of the eye(s). Non-limiting examples of an ocular characteristic include blood vessel architecture, color and reflectance, ischemic spots, nerve fiber layer loss, choroidal infarcts, Eischnig's spots exudates, pupil size, change in pupil size, and hemorrhages. An altered ocular characteristic can be the result of damage, exposure to a toxin, or a diseased state.

The term "disease state," optionally referred to simply as "disease," is intended to encompass not only the meaning as commonly understood by those skilled in the art to which this invention belongs but also conditions not necessarily pathological in nature. For purposes of this invention, a disease state is any condition the existence of which results in an alteration to one or more ocular characteristics in the subject. Non-limiting examples of a disease state include biological toxin or chemical agent exposure, systemic hypertension, internal trauma, inadequate nutritional status, and altered cognitive state. Biological toxins and chemical agents include, but are not limited to: organophosphates, cyanide, carbon monoxide, and botulinum toxin. For purposes of this invention, a disease state can also be caused by some type of injury or trauma to the subject.

The present invention relates to a device and methods of diagnosing and classifying a diseased state in a subject. Methods of diagnosing the diseased state preferably includes, in general, the steps of: 1) examining the subject's eye(s), utilizing the device of the present invention, to determine whether the subject exhibits an ocular characteristic indicative of the diseased state, and if so 2) evaluating any ocular characteristic to further classify the diseased state, including the severity. One or more altered ocular characteristics can indicate the existence of the diseased condition in a subject.

The non-invasive device and methods of the present invention for determining disease or damage in a subject utilize changes in the eye, for example, changes in ocular features to determine the presence and/or magnitude of disease or damage in patients. The eye is a privileged end-organ and is the only place in the body where microvascular networks can be directly observed. Changes in the vessels, arteries and arterioles of the eye, pupil size and rate of pupil constriction may correspond with exposure to toxins and damage and/or disease.

In a presently preferred embodiment, ocular characteristics of a subject's eye are evaluated by first quantifying the ocular characteristic under consideration. For example, the diameter of the subject's pupil can be measured and assigned a numerical character corresponding to the diameter. This number, or quantity, can then be compared easily to a normal pupil under similar conditions, which also has been quantified by assigning an appropriate numerical character. In another embodiment, blood vessel colorization may also be measured. The norm for the ocular characteristic, in the case of this example the normal pupil size or normal colorization, is established for each subject being examined. In an alternate embodiment, average normal values can be established for different populations and sub-populations. The subject's pupil size or vessel colorization may also be measured before, during and after light flashes of varying intensity and duration. A subject's quantified ocular characteristic data can then either be compared to his or her personal normal value, or it can be compared to an average normal value established for a population to which the subject belongs (e.g., FIGS. 5 and 6). In so doing, a person examining a subject's eye can determine whether one or more ocular characteristics have been altered.

Multiple images, types of images and regions of the eye may be examined. In one embodiment of the invention, images acquired from one eye of the patient may be sufficient. In other embodiments, images from both eyes may be used or compared to each other.

In an embodiment of the present invention, the subject's eyes are examined passively, where the Examiner may manipulate the eyes to obtain an ocular image but the subject is not required to voluntarily act or react to external stimuli. The subject's eyes are evaluated using one or more ocular characteristics (for example, arteriolar width, focal constrictions, hemorrhages, exudates, cotton wool spots, pupil size and rate of constriction, etc.). By analyzing these ocular characteristics, a diagnosis may be made by a processing unit or similar means employing a decision tree or algorithm.

The device and methods of the present invention may be used in conjunction with "dyes" or other chemicals injected into the blood stream or applied to the surface of the eye or its surrounding tissues. The changes in the eye caused by the dye could provide indications of the health of the vasculature and tissues. Examples of this include, but are not limited to, current uses of fluorescein or other chemicals applied to the surface of the eye or orbit or injected to reveal vessels of the eye, retina, pupil and other ocular tissues. The externally visible portions of the eye and its surrounding tissues or features within the eye may then be monitored using the methods of the invention.

The device and methods of the invention are capable of measuring changes in the eye and correlating these changes with a diseased state. Changes in the following ocular characteristics may be measured and analyzed by the device and methods of the invention:

Retinal (Fundoscopic) Changes

The retinal vessels change in several distinct ways as a result of disease or damage. These changes include vessel size, shape and color. Flame shaped hemorrhages may appear in the nerve fiber layer of the retina. Circular hemorrhages become visible on the deeper retinal layers. Cotton wool spots (the accumulation of axoplasmic products due to hypoxia of axons) may cause the death of nerve fibers. In addition, leakage around the vessels may occur as the blood-retinal barrier breaks down. This leaking fluid may also result in edema around the disk of the optic nerve.

Chorodial Vessel Changes

The chorodial vessels are best viewed directly through the aid of dyes (such as fluoroscein and indocyanine green). The choroid receives considerable sympathetic innervation. Therefore, vasoconstrictive factors, i.e., angiotensin II, adrenaline and vasopressin (related to sympathetic activity in the cardiovascular system) are likely to affect the choroidal system earlier and/or more severely than retinal vasculature. Narrowing and leakage of the chorodial vessels can be observed through the use of dyes. The areas of leakage often appear as elongated yellowish spots in the fundus and are termed Elschnig's spots.

Optic Nerve Vessel Changes

The optic nerve contains the only true arteries of the eye. The arteries can develop atherosclerosis, which is visible opthalmoscopically. More commonly, however, one observes optic disk swelling or edema followed by optic disc pallor and optic disc ischemia. The ischemic changes observed in the optic nerve may be secondary to the changes in choroid as much of the nourishment of the optic nerve comes from the choroid.

Changes in Other Ocular Blood Vessel Coloration

Ocular blood vessel coloration preferably is another ocular characteristic evaluated when examining a subject's eye. Ocular blood vessel coloration preferably is examined to assess whether there has been a significant change, e.g., increased brightness or darkness, of the blood in the ocular blood vessels. Non-limiting examples of times at which it may be desirable to analyze a subject's pupil size are after suspected or possible exposure to a biological toxin or chemical agent, when the subject displays symptoms of or is at risk for developing systemic hypertension, when there is a possibility that the subject has suffered a blunt head injury, as part of a routine check-up or health screening, and after the occurrence of any other event likely to induce a disease state in the subject. Ocular blood vessels include, but are not limited to: arteries, veins, venules, capillaries, and arterioles.

Figure 8:
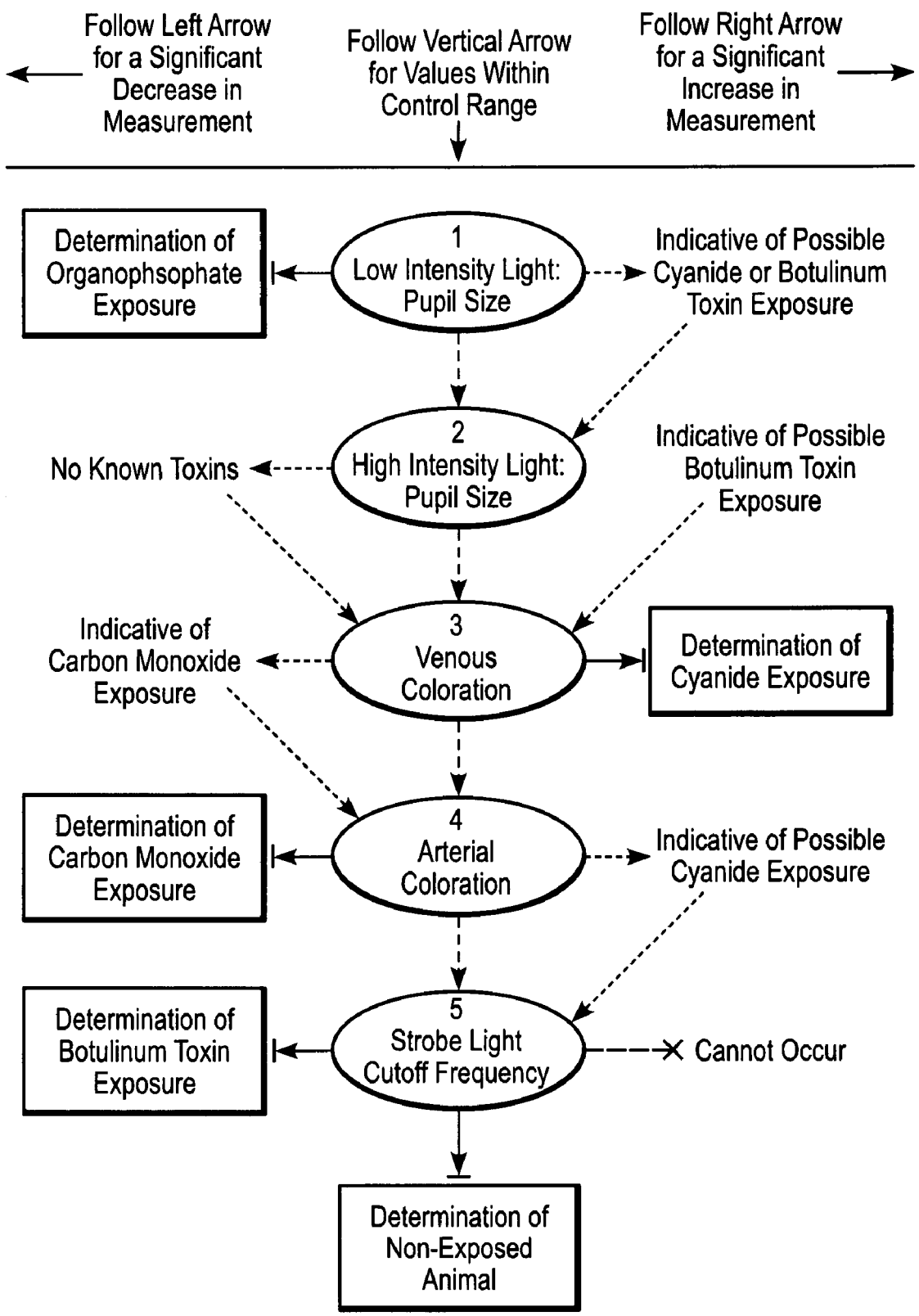
FIG. 8 is a flow chart showing an exemplary embodiment of a method for diagnosing exposure to a biological agent or chemical threat.

To determine whether there has been a significant change in ocular blood vessel coloration, a baseline, or "normal," color preferably is first established for certain ocular blood vessels, e.g., retinal veins and arteries. Normal coloration preferably is established for each subject using the device of the present invention for imaging the internal regions of the eye under non-mydriatic conditions. Alternatively, an average (or baseline) ocular blood vessel coloration for a given population to which the subject belongs can be used as the normal vessel coloration for all members of the population. While examining the subject's eye, images of the internal regions of the subject's eyes can be obtained for comparison purposes. As shown in FIG. 8, a significant increase in the brightness of the retinal veins can indicate possible cyanide exposure. Significantly increased brightness of the retinal veins, combined with an increase in pupil size in low intensity light, can lead to a definitive diagnosis of cyanide exposure. In contrast, a significant decrease in brightness of the retinal veins can indicate possible carbon monoxide exposure. A diagnosis of carbon monoxide exposure can be confirmed by analyzing retinal artery coloration. A significant decrease in brightness of the retinal arteries, combined with a significant decrease in retinal vein brightness, can lead to a definitive diagnosis of carbon monoxide exposure.

Arterial coloration also can be useful as a secondary characteristic for assessing the severity of cyanide exposure. Whereas retinal vein coloration is affected at relatively low doses of cyanide exposure, retinal artery coloration is not affected until the subject has been exposed to relatively high doses of cyanide. This differential sensitivity of the retinal veins and arteries is a useful method for determining the severity of cyanide exposure. A similar phenomenon exists with carbon monoxide exposure. Whereas retinal artery coloration is affected at relatively low doses of carbon monoxide exposure, retinal vein coloration is not affected until the subject has been exposed to relatively high doses of carbon monoxide. An analysis of the differential response of retinal arteries and veins thus also can be useful for determining the severity of carbon monoxide exposure.

Changes in Pupil Size

Referring generally to FIG. 8, pupil size preferably is one of the ocular characteristics evaluated when examining the subject's eyes. The pupil(s) preferably are evaluated to assess whether there has been a significant increase (dilation) or decrease (miosis) in the diameter of the pupil(s). Non-limiting examples of times at which it may be desirable to analyze a subject's pupil size are after suspected or possible exposure to a biological toxin or chemical agent, when the subject displays symptoms of or is at risk for developing systemic hypertension, when there is a possibility that the subject has suffered a blunt head injury, as part of a routine check-up or health screening, and after the occurrence of any other event likely to induce a disease state in the subject.

To determine whether there has been a significant change in pupil size, a baseline, or "normal," pupil size preferably is established. A normal pupil size preferably is established for each subject by measuring the diameter of each subject's pupil(s) under a controlled setting, i.e., controlled lighting, etc. Alternatively, an average (or baseline) pupil size for a given population to which the subject belongs can be used as the normal pupil size for all members of the population. While examining a subject's eye, the diameter of the subject's pupil preferably is measured. The subject's pupil(s) preferably are evaluated in two settings—one with low intensity light (for example about 1.7 $cd/m^2$), and the second with high intensity light (for example about 80 $cd/m^2$). As shown in FIG. 8, a significant decrease in pupil size (pupil contraction or "miosis") in low intensity light can indicate exposure to a toxin, such as an organophosphate.

The extent of exposure can be evaluated by examining whether the subject's pupil(s) retain their ability to contract and dilate in response to altering light conditions (pupillary light reflex). Pupil(s) retain their pupillary light reflex when subjects are exposed to relatively low levels of an organophosphate. The pupillary light reflex is eliminated, however, when subjects are exposed to relatively high levels of an organophosphate. After organophosphate exposure is diagnosed, the extent of the exposure can be determined by repeatedly exposing the affected subject's pupil(s) to a high intensity light followed by a low intensity light. Those subjects in which the pupillary light reflex has been eliminated (or greatly reduced) have been exposed to relatively high levels of an organophosphate. In contrast, those subjects in which the pupillary light reflex remains intact have been exposed to relatively low levels of an organophosphate. This aspect of the invention can be especially useful as a means for triaging casualties in military field operations where masses of military personnel can possibly be exposed to chemical warfare agents at the same time. As shown in FIG. 8, a significant increase in pupil size (dilation) in low intensity light can indicate possible cyanide or botulinum toxin exposure. Pupil dilation in high intensity light is a further indicator of possible botulinum toxin exposure.

Changes in Strobe Light Cutoff Frequency

Strobe light cutoff frequency preferably is another ocular characteristic evaluated when examining a subject's eye. In normal, i.e., healthy or disease-state-free, subjects, there is a maximal frequency at which the pupillary light reflex can function. This frequency is limited by the frequency at which nerve impulses denoting a light flash can travel from the retina, through the pupillary light reflex loop, and back to the muscles controlling pupil size for effect. For comparison purposes, this value is considered the normal (or baseline) strobe light cutoff frequency. The normal strobe cutoff frequency preferably is determined empirically for each subject. Alternatively, an average (or baseline) cutoff frequency for a population to which the subject belongs can be determined and used.

In an additional embodiment of the invention, as an alternative to strobe cutoff-frequency, analysis of pupillary latency may also be used to determine certain ocular characteristics. This methodology involves measuring the amount of time elapsed between the initiation of a light flash and the initiation of pupillary constriction, thus providing another quantitative evaluation of the amount of time required for impulses denoting a light flash to travel from the retina, through the pupillary light reflex loop, and back to the muscles controlling pupil size. An imager with a faster frame rate (more images acquired per second) is required for accurate analysis via this methodology.

At a pre-determined time, strobe cutoff frequency is obtained for comparison purposes. A significant decrease in the maximal response frequency after over-stimulation with high intensity light flashes can indicate botulinum toxin exposure. Strobe cutoff frequency preferably is examined using a tunable strobe device for applying various intensities of light at known frequencies.

Table 1 is a list of exposures that may be detected by changes in the human eye. This list does not include all possible exposures, but rather it is a collection of typical exposures that could be detected by the device of the present invention.

TABLE 1

Exposures that may be detected by changes in the human eye

| Chemical | Cyanides | Toxins |
|---|---|---|
| Organophosphate nerve agents Sarin VX Tabun Soman Pesticides | Potassium Sodium | Botox Ricine Endotoxins |

| Explosives | General Health | Occupational Health |
|---|---|---|
| RDX TNT Nitroglycerine | Internal Trauma Systemic Hypertension Diabetic Retinopathy Head Trauma Diving Decompression Fatigue Assessment Immune Response | Gasses Carbon Monoxide Carbon Dioxide Arsenic |

| Heavy Metals | Controlled Substances | Other |
|---|---|---|
| Cadmium Mercury Lead Uranium | Drugs Methamphetamines Antidepressants Tobacco Depressants Alcohol | Toxic Industrial Chemicals Concussions Blood Oxygen Thermobarics |

The current invention utilizes an ocular technology (Ocular Scanning Instrumentation, OSI) developed by Eye Marker Systems, Inc., Morgantown, W. Va. The OSI technology employs non-invasive imaging of ocular characteristics that can quickly analyze a human eye to determine if the subject has been exposed to various harmful conditions or is suffering from a diseased state. The OSI will capture images of the subject's eye to quickly compare it to predefined data comprised of thousands of laboratory test results. The OSI uses this comparison to help determine the level of medical attention needed. The OSI will use non-visible light to create images and visible light to stimulate the subject's eye. The combination of the two lights will vary depending on the type of scan. The instrumentation is capable of evaluating, analyzing and quantifying several ocular characteristics such as pupil size and motility (light reflexes), corneal abnormalities (clouding, blistering and ulcerations) and blood coloration/oxygenation (including arterial and vein discrimination).

For purpose of illustration, the present invention is shown in the drawings described below. FIG. 1 is a schematic diagram illustrating an embodiment 100 of the claimed ocular scanning device. In one embodiment of the invention, the ocular scanning device of the present invention is a stationary apparatus appropriate for use in a physician's office or laboratory. In another embodiment, the device consists of a smaller handheld device capable of being carried to various locations and used outside of the normal office or laboratory setting. In certain embodiments, the device 100 is enclosed in a hard outer storage case. This storage case provides a housing to protect the imaging system when the system is moved or transferred between locations. The case is preferably water resistant and must protect the device from weather, mobility hazards and outside light. In an additional embodiment of the invention, the storage case is designed to be grasped by the human hand.

Figure 7:
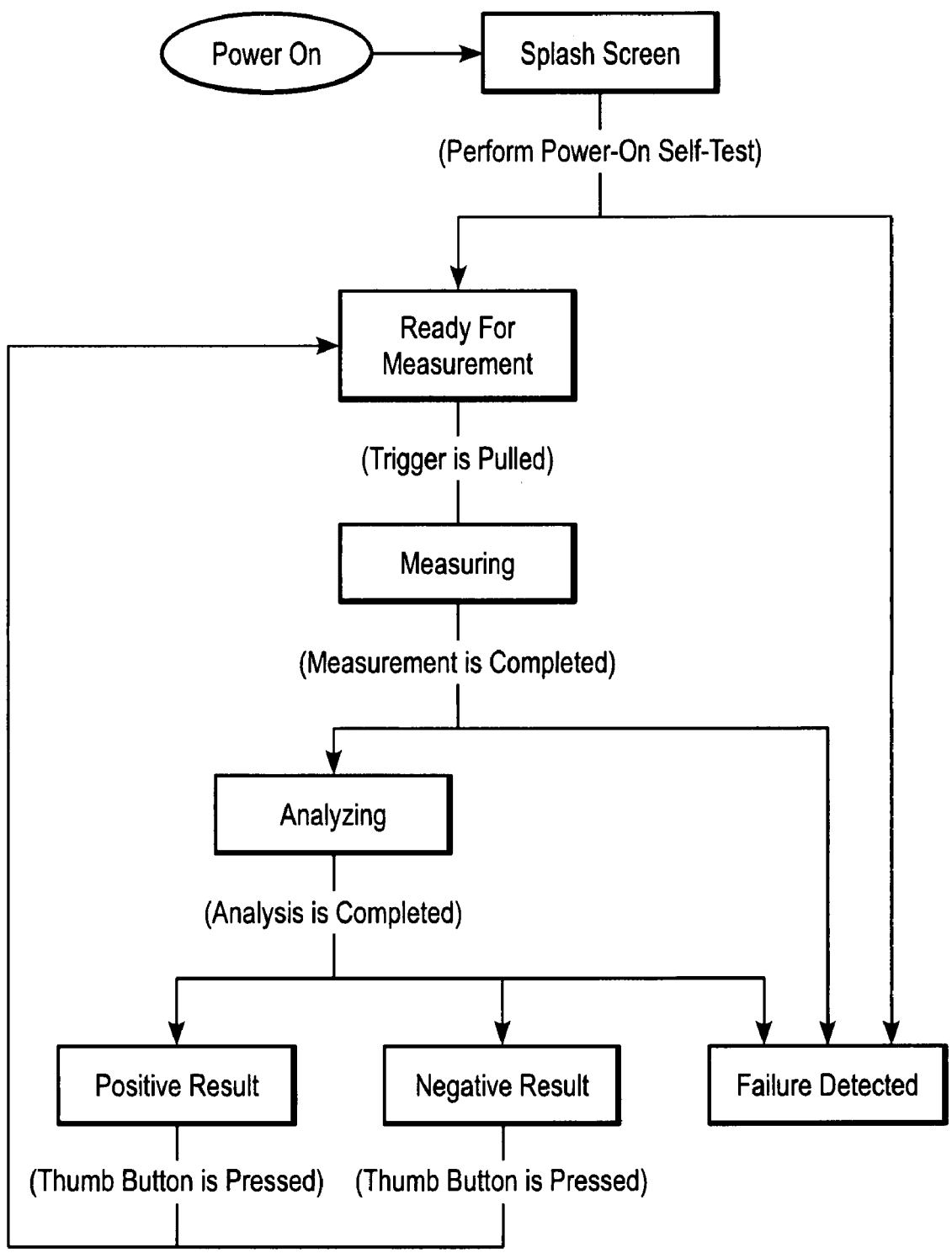
FIG. 7 is a flow diagram illustrating one embodiment of a display screen operation.

The device consists of a base 110, containing a battery compartment for a power source. The device may utilize any type of battery, for example alkaline or rechargeable batteries. In alternate embodiments, base 110 may contain electronics capable of utilizing electrical (A/C) power. In addition, base 110 may be secured to a table or bench to allow for stationary use, or may remain unsecured for portable use. A handle 120 is suitable in size and shape to fit comfortably in the hand of the operator. A toggle switch activator 130 allows the operator of the device to scroll through user menus, activate measuring functions, view results and reset the device for a subsequent measurement. A goggle-shaped patient interface plate 140 is shaped to comfortably fit over the patient's eyes and to limit ambient light from entering the device. A LED display 150 displays directions for the operator and allows for user input. LED display 150 asks for user input to begin measurements and analysis and to clear results in preparation for the next measurements. A non-limiting example of the function of this LED display screen is found in FIG. 7. The operator responds to the prompts from LED display 150 by pressing on toggle switch activator 130.

Figure 2:
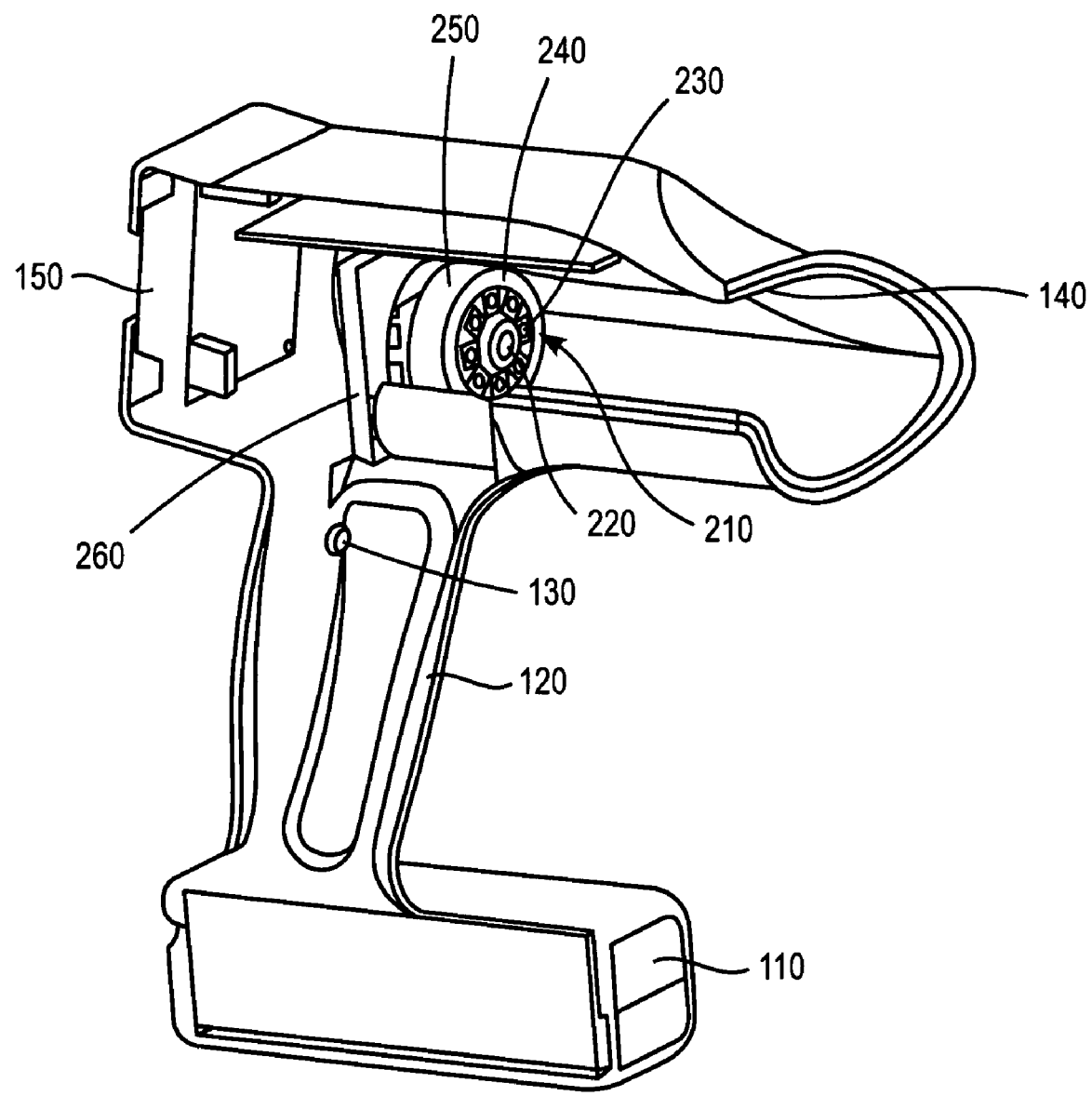
FIG. 2 is a schematic drawing illustrating an internal view of one embodiment of the device of the invention.

FIG. 2 illustrates an internal view of the claimed apparatus 100. The apparatus consists of optic assembly 210, which focuses emitted light onto the eye of the patient and then focuses the resulting image into the Chip Charged Coupled Device (CCD, see below). This is plausible because the different measured characteristics will generally be found at different ranges (distances) from the CCD due to the location within the eye and the curvature of the eye. Optic assembly 210 further consists of a lens 220 and a series of light emitting diodes (LEDs) 230. LEDs 230 can emit light at varying intensities and at different wavelengths. LEDs 230 have 0-100% adjustability and both white light and infrared capabilities. Near infrared emission can be performed continuously, while white light can be emitted in sequence as controlled by the algorithm. An optic holder 240 holds and rotates the LEDs. A 3-Chip Charged Coupled Device (CCD) imaging system 250 captures images of the eye. The CCD imaging system consists of two parts, the pupil imaging system and the retinal imaging system (not shown). Each of these imaging systems preferably have separate systems to control resolution/color depth and illumination. Once light is captured, the CCD device converts the image into a group of digital signals which may be converted into an images and further analyzed. A linear activator 260 provides movement of the optic assembly for focusing.

Figure 3:
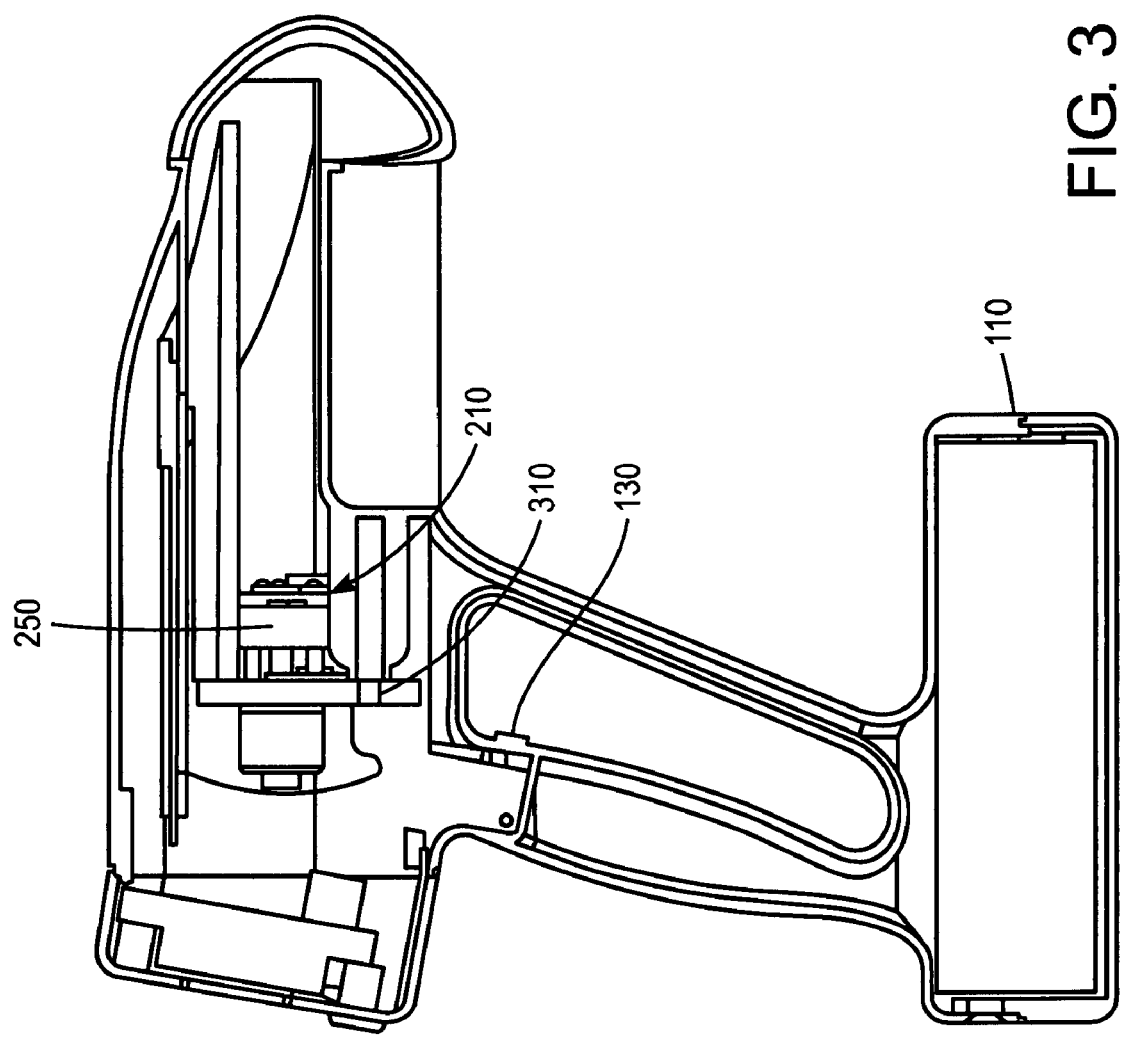
FIG. 3 is a schematic drawing illustrating a second internal view of one embodiment of the device of the invention.
Figure 11:
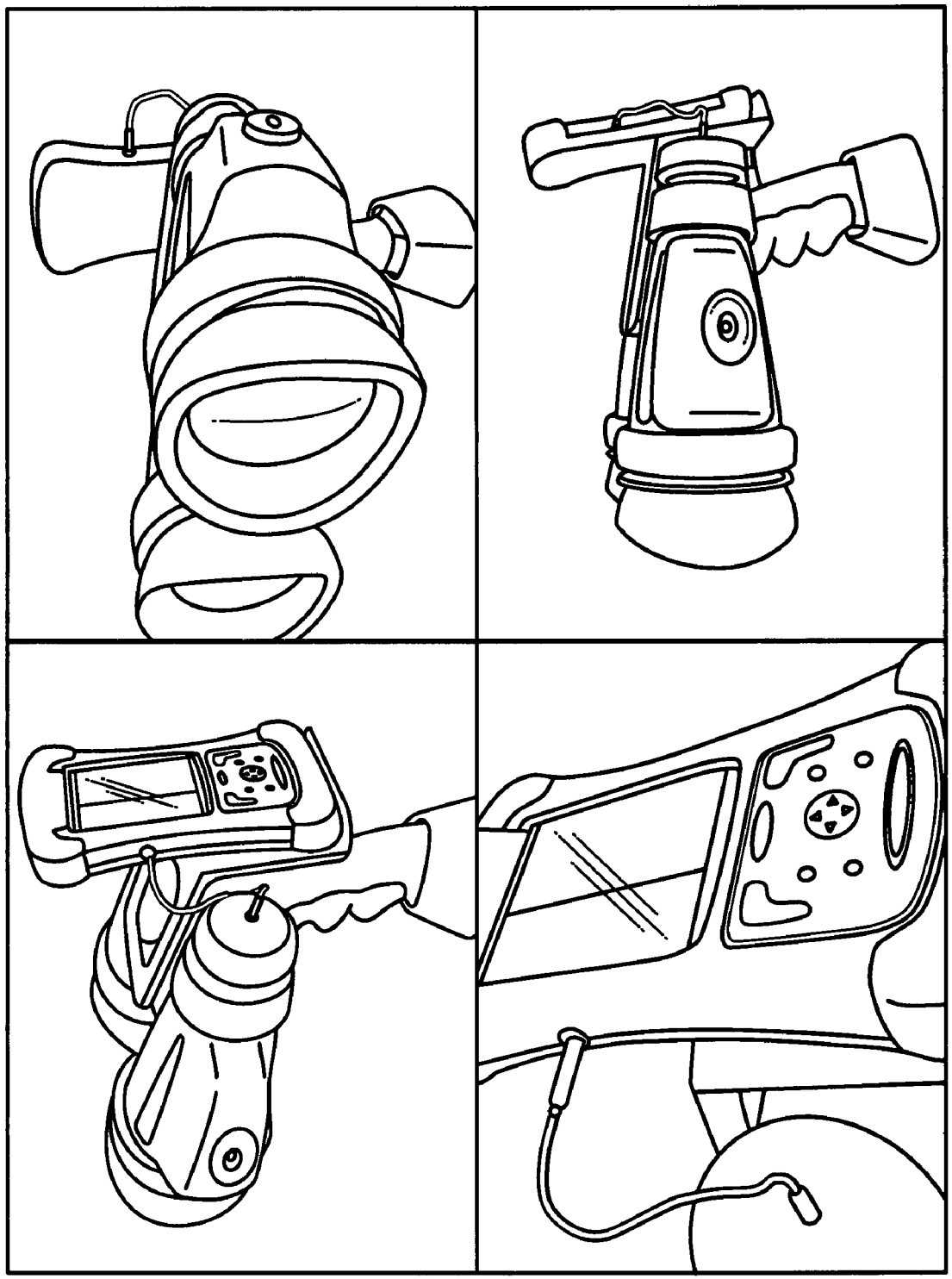
FIG. 11 is an additional representation of a hand-held (single hand) embodiment of the device of the invention.
Figure 12:
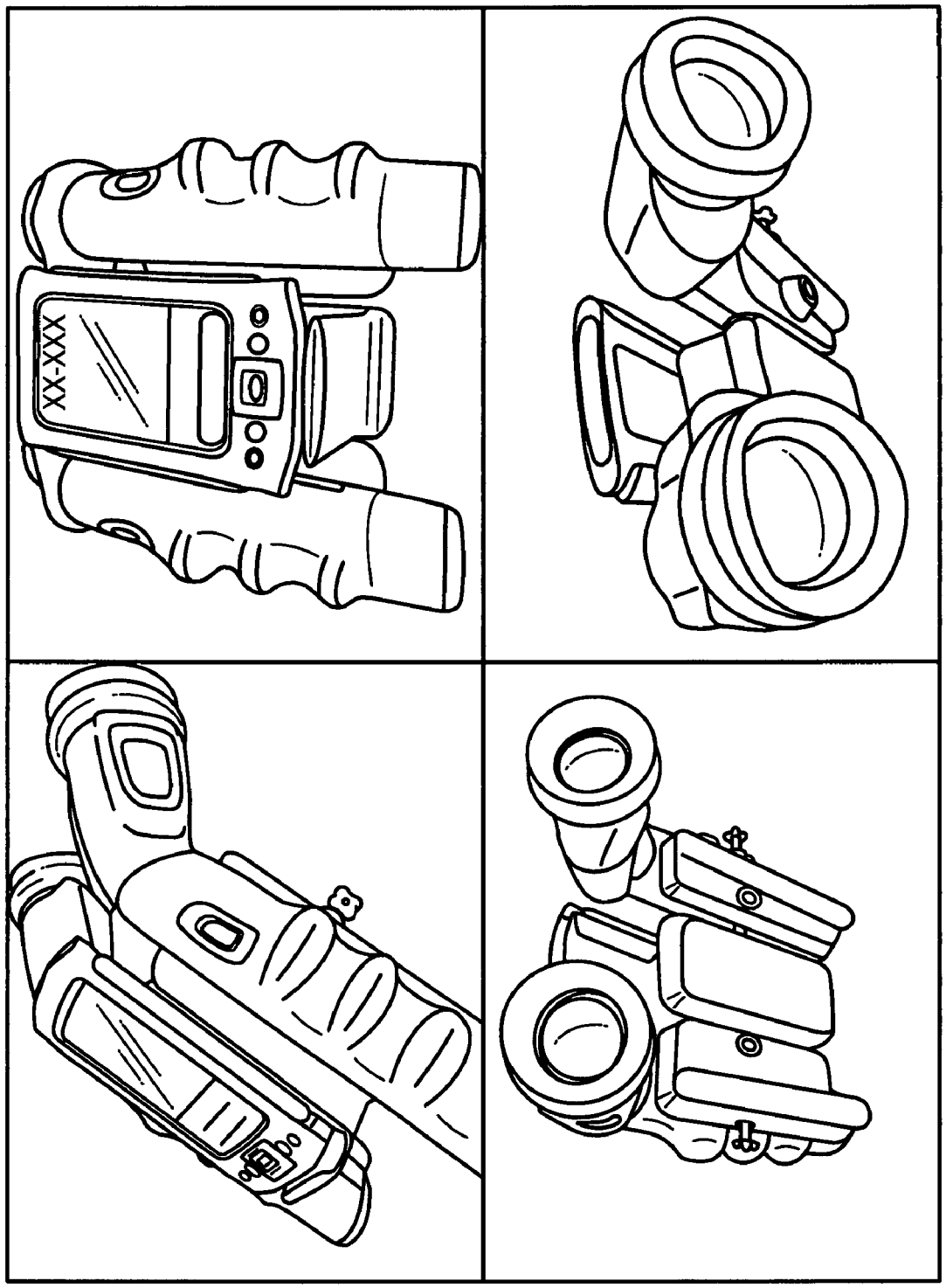
FIG. 12 is an additional representation of a hand-held (two hand) embodiment of the device of the invention.

FIG. 3 further illustrates the internal view of one embodiment of the claimed device. Slide-bar 310 allows for the movement of the optic assembly to facilitate focusing of the ocular image. In one embodiment of the invention, the claimed device measures the ocular characteristics in a single eye during each reading. In an alternate embodiment, the device measures ocular characteristics in each eye simultaneously. The device may measure the same characteristic in each eye, or measure two different characteristics. The claimed device may also be configured as a single-handed portable unit (FIG. 11), or a two-handed portable unit (FIG. 12).

After acquiring an ocular image, the image can be processed using a computer program or automated device. The processing step is followed by the extraction of the ocular features from the rest of the ocular image. This extraction can be performed on the device used for processing the ocular image or may utilize a separate computer program or automated device.

The ocular images may be analyzed via an automated method through the use of algorithms on a computer subsequent to uploading. The automated methods of the invention will use algorithms utilizing multiple image process techniques for analyzing the images generated by these systems. The algorithms will relate the appearance and extent of vessel changes, pupil changes and other abnormalities to a diseased state or toxin exposure.

The algorithms may be capable of, in an automated fashion, searching for alterations in the ocular images. Suitable computer algorithms preferably have the ability to: (1) accurately and sensitively identify the existence of ocular abnormalities; (2) accurately specify the type and extent of such abnormalities; and (3) correlate such findings to the diseased state of an individual. The automated method may provide a much more advanced capability for abnormality detection. Through automated processing techniques and the removal of qualitative evaluation, greater information may be derivable from the images.

The methods of the invention also include the classification of the ocular features. The classification comprises different ways to group or stage the ocular image as either diseased or healthy. The classification may comprise placing the ocular image into a classification of groups based upon the measurement of various physiological characteristics. Further, the classification may comprise comparing the ocular image to an algorithm of disease symptoms. The algorithm of disease symptoms comprises ocular diseased changes: changes in size, shape, and color of ocular vessels, changes in pupil size and rate of constriction, hemorrhages, cotton wool spots, leakage, hard exudates, and edema. Vessels may also show disease symptoms, especially when a dye is used.

In a preferred embodiment, the automated methods of the invention comprise algorithms utilizing multiple image process techniques for analyzing the images generated by these systems. The images may then be carefully analyzed to determine the disease or damage status in patients. Finally, the findings may then be statistically correlated with other criteria to classify the patient.

Figure 4:
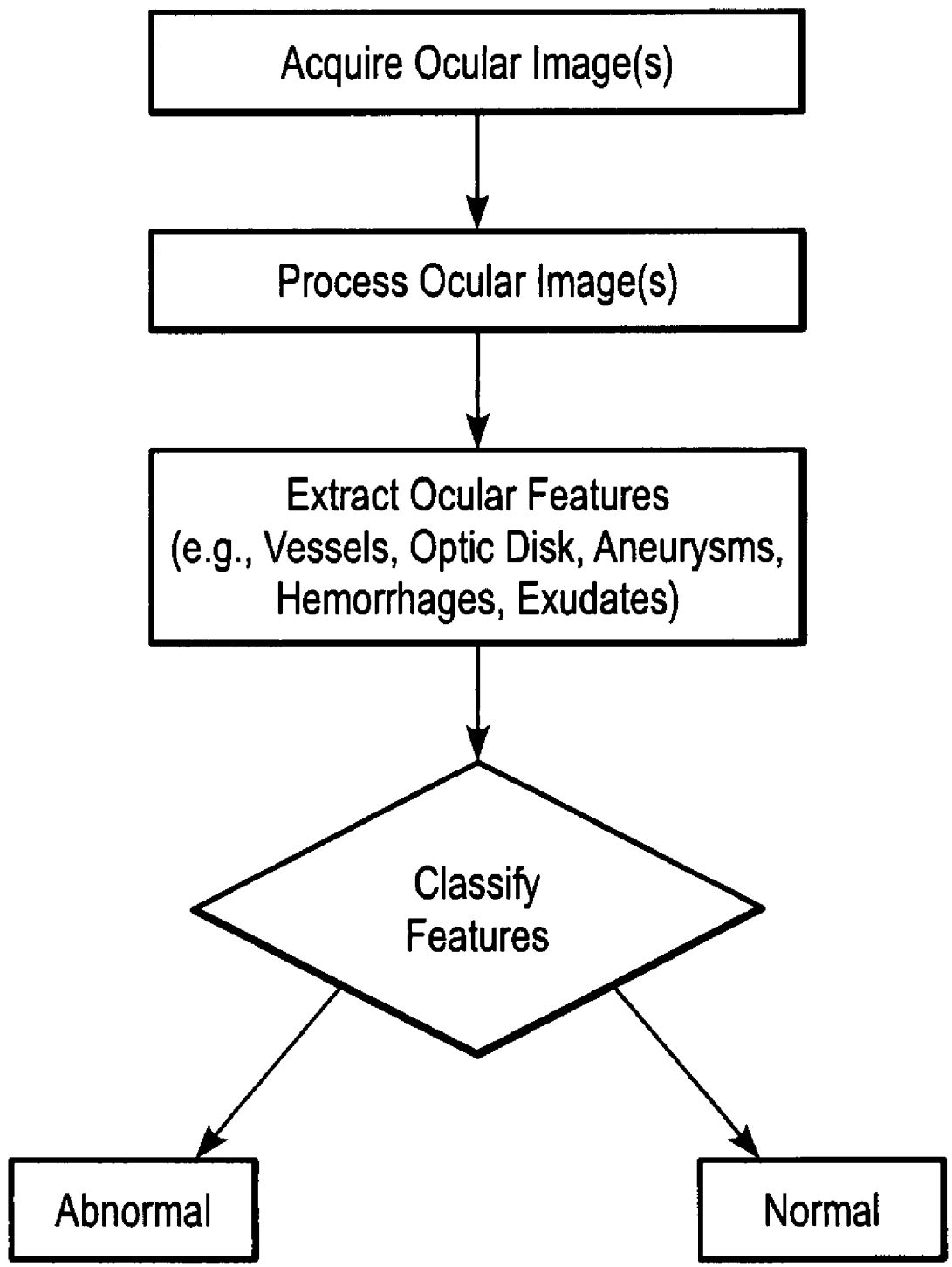
FIG. 4 is a schematic view of the steps in a method for determining the presence of a diseased state in an individual patient.

In one embodiment of the present invention, the ocular images are analyzed through the use of algorithms specific for the physiological characteristic in question. The automated system of the invention makes a determination as to the status of the diseased state based upon the acquired ocular images. This method is illustrated in FIG. 4. Here, the methods of the invention are used to classify extent of disease or damage in a subject. In the first step of the method involves acquisition of the subject's ocular image. The second step involves processing of the ocular image. Next, the ocular images are extracted and the features classified. The classification is based upon established criteria of ocular abnormalities and damage. The extraction and classification steps are based upon algorithmic quantification and interpretation. The features are then grouped as "abnormal" or "normal" based upon the outcome of the classifications steps. Abnormal features may be further classified based upon their clinical presentation.

Figure 6:
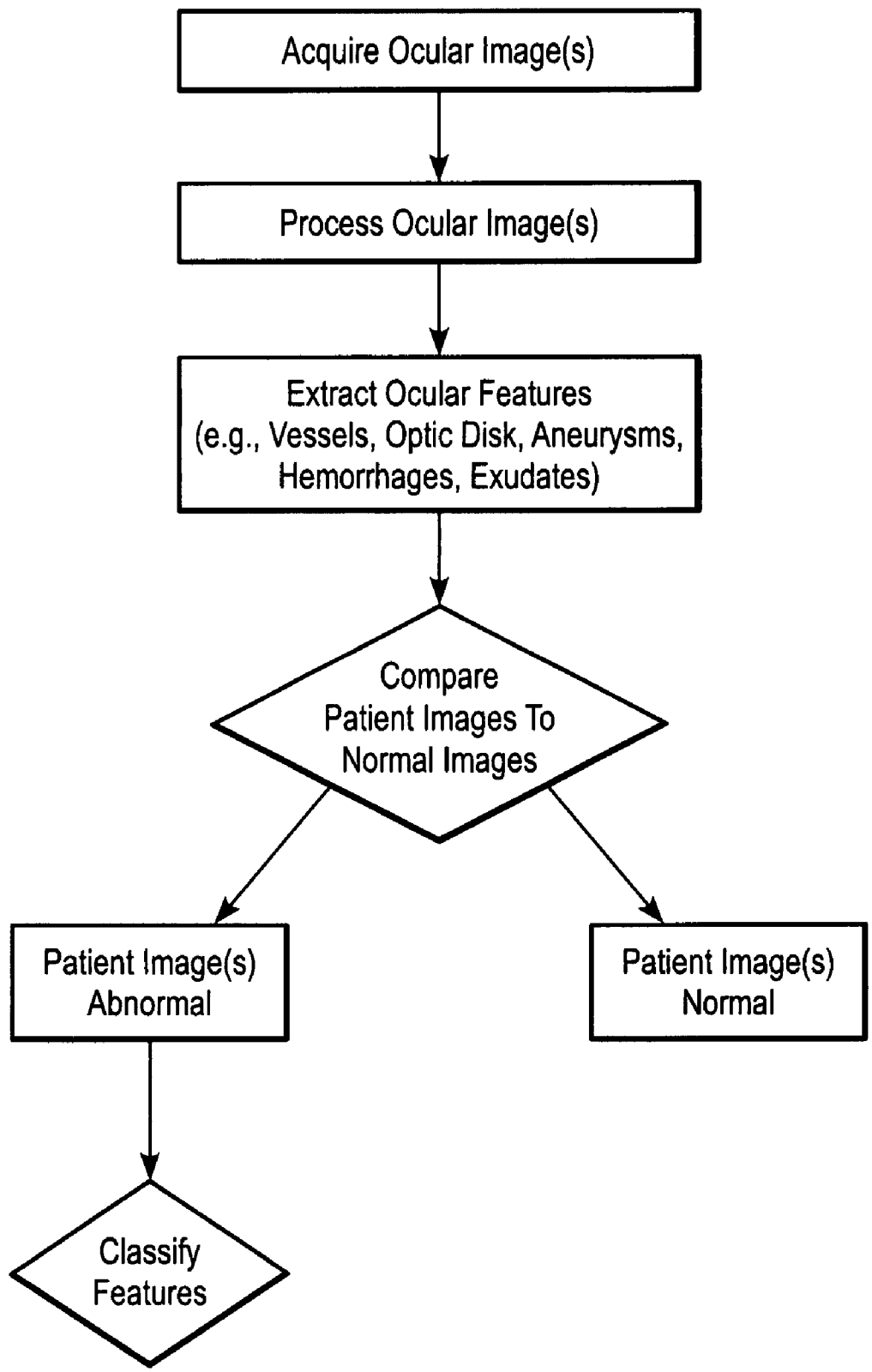
FIG. 6 is a schematic view of the steps in a method for determining the presence of a diseased state in a patient when compared to a non-diseased patient.

In an additional embodiment, the ocular images may be compared to standard photographs in a collected database, as illustrated in FIG. 6. The images in the database represent "normal" ocular features, i.e., those obtained from a non-diseased or damaged population. The subject's acquired image(s) are classified as either abnormal or normal based upon comparison to quantifiable criteria obtained from a normal sample as contained in the database. Subject's with abnormal images may be identified for further evaluation or given immediate medical attention if needed.

Figure 5:
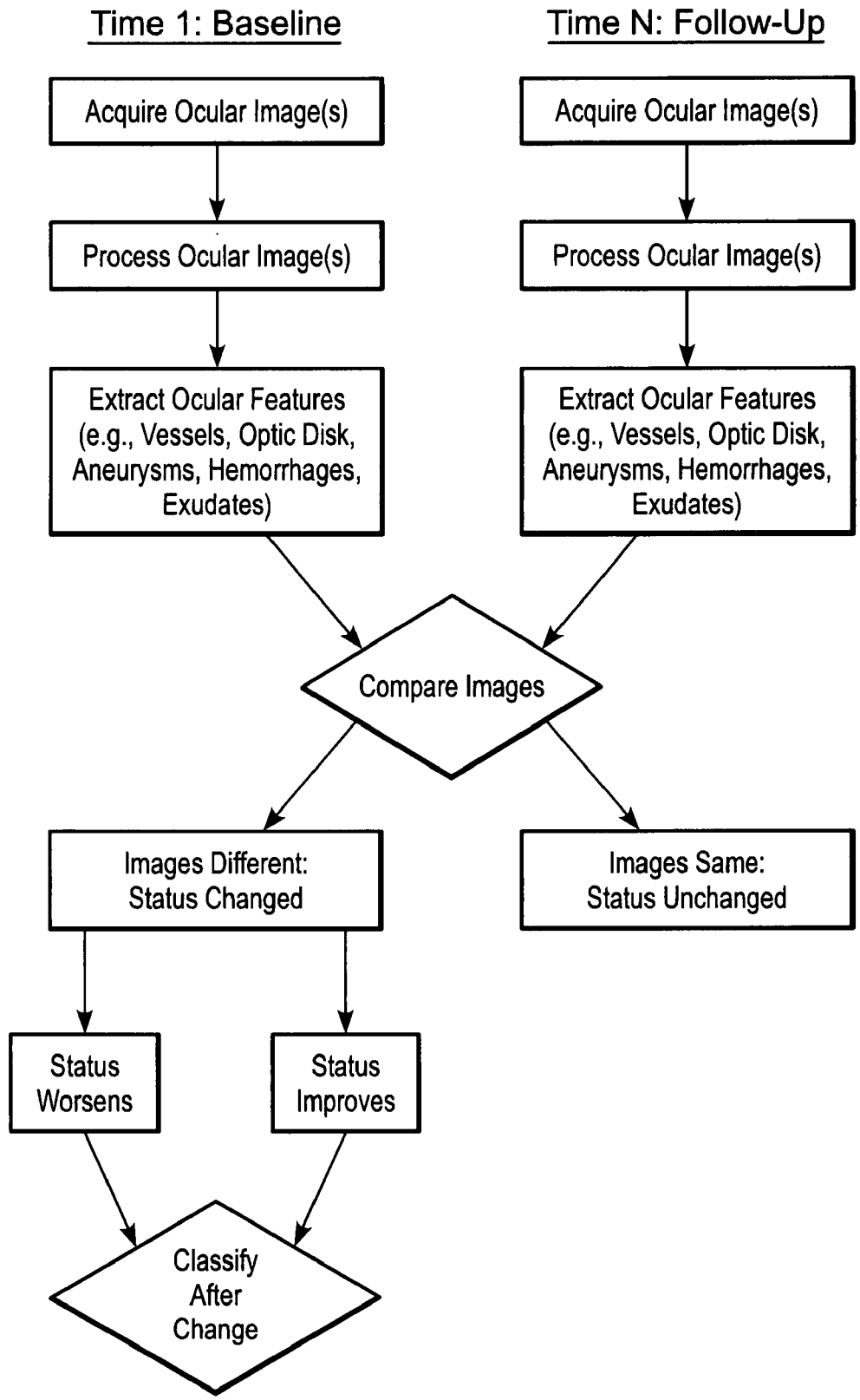
FIG. 5 is a schematic view of the steps in a method for determining progression of a diseased state in an individual patient.

It will be appreciated that the invention may also be employed advantageously to provide for periodic monitoring of subjects at intervals of days, weeks, months or years for comparison purposes to determine if meaningful changes have occurred over time. This embodiment of the invention is illustrated in FIG. 5. This figure illustrates steps in a method for determining the progression (or regression) of a diseased state in a patient. To determine whether there has been significant change in an ocular characteristic, a baseline, or initial reading is first established for the characteristic. Alternatively, an average (or baseline) ocular characteristic reading for a given population to which the subject belongs can be obtained for comparison purposes. In this embodiment, the patient's ocular features are classified on a first visit as either diseased or healthy and then subsequent follow-ups allow the monitoring of change in the ocular features. Based upon the initial or previous classification and analysis of ocular features, subsequent employment of the current method could be used to monitor progression or regression of disease or damage status based upon stasis, worsening, or improvement of ocular abnormalities resulting from or concomitant with disease. This aspect of the method would serve to evaluate (1) the efficacy of any therapies initiated since previous ocular analysis, (2) patient compliance with initiated therapies, and/or (3) the need for alternative or additional therapies. Abnormal features may be re-classified based upon their changed clinical presentation.

Despite the difficulties in evaluation ocular signs in diseased or damaged states, the present invention offers improvement for the utility of ocular signs in the evaluation of disease or damage and subsequent therapeutic intervention. First, the last decade has seen the development of several new and more powerful strategies and techniques for examination of the eye. Second, as technology has advanced and become far more cost effective, the feasibility of developing automated algorithms for evaluating these ocular findings has emerged. Third, through automation, the concurrent evaluation and interpretation of multiple ocular characteristics may be more thoroughly and efficiently combined to provide increased diagnostic capability and reliability without the need for specialized training. Finally, via an automated technique of quantitative and statistical evaluation of ocular characteristics more precise and accurate alterations may be identifiable which will aid in pathology recognition, allow more thorough examination of potential changes, and subsequently provide increased diagnostic capabilities through ocular evaluation.

The following examples are provided to illustrate certain embodiments of the invention, but are not intended to limit the invention. The examples and embodiments described herein are illustrative, but not limiting, of the probes, methods and kits of the present invention. Other suitable modifications and adaptations of the variety of conditions and parameters normally encountered in typical laboratory and which are obvious to those skilled in the art are within the spirit and scope of the invention described herein.

Example 1

Analysis of Exposure to Organophosphates, Cyanide, Carbon Monoxide and Botulinum Toxin The following experiment details the diagnosis of exposure to various chemical and biological threat agents, including organophosphate nerve agents, cyanide compounds, carbon monoxide and botulinum toxin. The first step in the diagnosis is the identification of ocular biomarkers for each of the agents.

Many organophosphates (OPs), including tabun, sarin, soman, syclosarin, and VX, are nerve agents that can be used for chemical warfare. Other members of the OP group are commonly used as agricultural pesticides (e.g., Malathion, Parathion, Trichlorfon, etc.). The OPs share a similar chemical structure and are derivatives of phosphoric or phosphonic acids containing two alkyl groups and a leaving group. The primary pharmacological effect of the OPs is to inhibit the enzyme acetylcholinesterase (AChE) via phosphorylation of a serine hydroxyl group in the active site of the enzyme. AChE normally functions to quickly destroy acetylcholine (ACh) in the synaptic cleft and thus terminate transmission of a nerve impulse. Inactivation of AChE results in the accumulation of ACh, which causes an initial enhancement and prolongation of cholinergic activity followed by depolarization blockade. The primary ocular biomarker for exposure to organophosphate nerve agents is a change in pupil size under low lighting conditions.

The cyanides, when compared to other lethal chemical warfare agents, are the least toxic. However, though these agents may be less potent in their lethality, they act very quickly and thus diagnosis and subsequent actions to combat their effects must commence promptly after exposure. The cyanides of military interest are the volatile liquids: hydrogen cyanide (HCN), cyanogen chloride (ClCN), and cyanogen bromide (BrCN). The pharmacological and toxicological effects of the cyanides (due to cyanide [$CN^-$]) are identical, but the cyanogens also are an irritant to the eyes and respiratory tract. Cyanide acts by combining with the ferric ion in mitochondrial cytochrome oxidase, preventing electron transport in the cytochrome system and, thus, bringing oxidative phosphorylation and ATP production to a halt. Though fully oxygenated, the cells cannot utilize the oxygen and thus increased demands are placed on anaerobic glycolysis. This results in lactic acid production/accumulation and eventual cell death due to histotoxic anoxia. A primary ocular biomarker for exposure to cyanide is fundal venous colorization/oxygenation.

Carbon monoxide (CO) is a colorless, odorless gas which comes from numerous sources. Part of CO's acute toxicity results from the fact that it essentially replaces the oxygen in the blood. Hemoglobin (Hgb), the oxygen carrying molecule of the blood, has an affinity for CO which is approximately 200-250 times greater than that for oxygen. The absorption of CO by the blood (creating carboxyhemoglobin) causes a leftward shift in the oxygen-hemoglobin dissociation curve, resulting in a decreased oxygen carrying capacity and impaired release of oxygen to the tissues. This, in turn, leads to cellular/tissue hypoxia. The relatively high affinity of Hgb for CO also results in a relatively persistent effect in individuals well after they've been removed from exposure to the gas.

Though carbon monoxide poisoning generally results from chronic exposure to lower levels of CO, there are many documented cases of acute poisoning. In addition, the relatively low level of toxicity and reversibility of CO poisoning has allowed more extensive human studies to be performed than with many other toxins. The brain and heart, by virtue of their high metabolic activity, appear to be the most rapidly affected sites of CO poisoning. Unfortunately, many of the early warning signs for CO poisoning are similar to common flu-like symptoms: headache, nausea, dizziness, etc. In cases of more severe poisoning, the clinical findings may be very similar to that of cyanosis (cyanide poisoning; see above). This is somewhat to be expected in that both carbon monoxide and cyanide deprive tissues/cells of the ability to utilize oxygen. However, the different pathways by which these toxins reach this physiological endpoint may be of use in the quick determination of the type of poison in the system. As described above, for cyanide poisoning the hemoglobin/blood is fully oxygenated but the cells are deprived the ability to utilize this oxygen. On the other hand, with CO poisoning the hemoglobin/blood is severely under-oxygenated due to the formation of carboxyhemoglobin. This altered level of blood oxygenation is discernable based upon the coloration of the blood which is primarily determined by hemoglobin and its level of oxygenation. Thus, the primary ocular biomarker for exposure to carbon monoxide is fundal arterial colorization/oxygenation.

Botulinum toxin is one of the most poisonous substance known to man with a single gram of the crystalline toxin possessing the ability to kill more than 1 million people. Because of this extreme potency and lethality, as well as its ease of production and transport, botulinum toxin poses a major bioweapons threat. Botulinum toxin is a protein neurotoxin produced by various subtypes of the bacterium *Clostridium botulinum*, an anaerobic, gram-positive organism. Unable to penetrate intact skin, botulinum toxin requires a wound, ingestion, or inhalation to exert its effects. Upon gaining access to the general circulation, botulinum toxin binds with extremely high affinity to peripheral cholinergic nerve endings at the neuromuscular junction and in the autonomic nervous system (preganglionic sympathetic and parasympathetic, postganglionic parasympathetic nerve terminals). Once in the target cell, the toxin acts as a zinc-dependent endoprotease, cleaving polypeptides that are essential for the exocytosis (release) of acetylcholine (ACh). Botulinum toxin is both highly selective for cholinergic neurons and long lasting—clinically significant responses may last from several months to a year.

The human data concerning botulinum toxin effects comes primarily from cases of food-borne (ingested) and wound exposure. The classic clinical features of botulism (the disease caused by botulinum toxin exposure) are symmetric cranial neuropathies (i.e., ptosis [drooping eyelids], weakened jaw clench, dysarthria [speech disturbances], and dysphagia [difficulty swallowing]), diplopia (double-vision) or blurred vision, peripheral muscle weakness, respiratory dysfunction, and gastrointestinal distress (nausea and vomiting). In addition, pupillary light reflexes are typically depressed or absent and the pupils are dilated (mydriasis). With time, peripheral muscle weakness will progress to flaccid muscular paralysis and death results from respiratory muscle paralysis. Though little is published regarding the bioterrorist or military use of botulinum toxin, it is believed that such an attack (food-borne or aerosolized) would yield similar symptoms presenting 12-72 hours after exposure. In the case of inhalational exposure, the clinical presentation would be identical but the gastrointestinal symptoms would likely be absent. The primary ocular biomarker for exposure to botulinum toxin is pupil motility in response to light challenge.

The present example provides a method of determining exposure to organophosphates, cyanide, carbon monoxide and botulinum toxin utilizing the claimed device. Images of the eye are captured a described above. The images are analyzed through the use of a diagnostic algorithm, which completes the automated detection and automation of the above-mentioned ocular characteristics.

External Eye Algorithms

The external eye (pupil) algorithms accurately measure the size of the pupil. The pupil must first be isolated within the image captured by the device of the invention. The pupil size (area) is then determined. Since the pupil is the darkest part of the eye, the image is thresholded based upon average color. Once averages are obtained, points above the average were made white and the remaining image is scanned, unaltered, for edges. Using a direct least squares fitting method, pupil areas are fit with approximated ellipses and the x- and y-radii of the approximate ellipse is then employed to calculate pupil surface area. A Gaussian filter is applied after color thresholding. This method is rapid, accurate and very tolerant of jagged edges and image imperfections.

An exemplary pupil algorithm is outlined in Table 2. Part I involves acquiring the pupil images from the claimed ocular scanning instrument and mapping preliminary light images. Part II involves the analysis of the first pupil image. Part III involves analysis of the second and subsequent images.

TABLE 2

Pupil Algorithm

| Step # | Direction |
|---|---|
| | Part I: Acquiring Images From The Claimed Device and Mapping Preliminary Light Images |
| 1 | The pictures of the pupil are saved to a directory |
| 2 | Load each picture into a bitmap sequentially. |
| 3 | Save the green values from the bitmap into a 2D array of integers (pixels) and smooth the image with a 5 × 5 Gaussian filter. |
| 4 | Set the two-pixel unfiltered border to a medium gray. |
| 5 | Find the average value of the matrix |
| 6 | Apply rate of change (ROC) map:<br>a. For each pixel, determine the average of the sum of the differences of the current pixel using the 5 × 5 matrix that has the current pixel as the center.<br>b. Record this value if this ROC value is above a threshold, otherwise set to 0, creating a map with white edges and most of the picture is black. |
| 7 | The system lights create circular reflections in the eye. They form a square that is always roughly the same distance apart, varying from the curvature of the eye. A patient with their eye centered in the viewing aperture and looking at the fixation target should have these reflections in the center of the pupil. At this point the code branches between the first picture analyzed and the rest of the pictures. |

TABLE 2-continued

Pupil Algorithm

| Step # | Direction |
|---|---|

Part II: Analysis of the First Pupil Image

| | |
|---|---|
| 1 | Search for the light reflections (the brightest points in the picture), leaving roughly spherical artifacts). |
| 2 | Look near each light reflection for the remainder of the reflection. |
| 3 | Mark the points as examined. |
| 4 | If the number of points exceeds a threshold (eliminating smaller reflections caused by the water below the eye), find the box bounded by the reflection pixels. |
| 5 | Record the center of this point. |
| 6 | If a point is recorded, look nearby for the other lights:<br>a. Search in 8 directions (0, 45, 90, 135, 180, 225, 270, 315 degrees).<br>b. If a pixel likely belonging to a light is found, find the rest of the light.<br>c. Determine the area of the light and store this value it if it is above threshold.<br>d. Find the largest box that is bounded by these points and record the center. |
| 7 | If at least one light has been found, search for the edges of the pupil:<br>a. Find a point at center of largest box bound by the lights.<br>b. If the number of lights is less than three, move out of line from the other points.<br>c. Search left/right above/below by a constant distance and take the darker of the pair.<br>d. Search in each direction, keeping track of the number of consecutive not-black pixels hit, and search along the direction until the picture bounds are hit, or a threshold of not-black pixels is reached. This skips small artifacts inside the pupil.<br>e. When the search is stopped, record the location of the last examined black pixel.<br>f. Repeat for the other directions |
| 8 | Find the largest box bound by these points. |
| 9 | Find the center of this new box, and record half the horizontal distance (x radius) and half the vertical distance (y radius). |
| 10 | Adjust for pupils that are partially out of the picture. |
| 11 | The pupil is round. If the x and y radius are more than 10% different from each other, increase the smaller to the larger. |
| 12 | Expand the search region to have a buffer zone of non pupil. |
| 13 | Adjust the buffer zone to ensure it stays within bounds. |
| 14 | Find the center of the search zone in case the zone was changed. |
| 15 | Adjusting for pupils that are partially outside the picture, find the pupil:<br>a. Starting from the left, record the top and bottom pixel determined as edge by a combination of comparison to the average and a ROC threshold. The middle third of the area is skipped to prevent artifacts from creating a false edge. Keep the union of the lists of top points and bottom points.<br>b. Starting from the top, record the left and right pixel determined as edge by a combination of comparison to the average and a ROC threshold. The middle third of the area is skipped to prevent artifacts from creating a false edge. Keep the union of the lists of left and right points.<br>c. Merge the list of vertical points with the list of horizontal points allowing duplicates. |
| 16 | Separate the x and y coordinates of the point list into separate arrays. |
| 17 | Fit an ellipse to the data using these new arrays. |
| 18 | Find and record surface area of the ellipse. |
| 19 | If the ellipse is too small to be a pupil:<br>a. Find mean x and y values of the lights.<br>b. Find the box made by going to the max radius (determined from control data) of the pupil from this mean point.<br>c. From top left corner, look for all points that based on a combination of comparison to the color average and ROC map, are determined to be edge.<br>d. If there are more than a threshold of points, find and record the mean x and y value of these points to use as a new center.<br>e. Rebound the search area with max pupil radius based on this new point.<br>f. Search for edge points.<br>g. Find the center again based on these points.<br>h. Filtering horizontally, keep the first and last pt on each line that registers as edge.<br>i. Go back to step 16. |
| 20 | If there was no ellipse record the surface area as −1. |
| 21 | The minimum and maximum dilation of the pupil and the rate of change of dilation over time are the variables used for the triaging decision. |

Part III: Analysis of the Second and Subsequent Pupil Images

| | |
|---|---|
| 1 | Starting from the center of the last ellipse found, search an area larger than the area of the last ellipse (for pupil expansion and eye movement). |
| 2 | Adjust search area to be within bounds of the picture. |
| 3 | Get the green value matrix from the picture. |
| 4 | Perform ROC of picture (same as Step 6 of Part I.). |
| 5 | Accounting for partially out of picture pupils, search outward from the center, stopping when determined to be at an edge. |

TABLE 2-continued

Pupil Algorithm

| Step # | Direction |
|---|---|
| 6 | This trace can be stopped by artifacts in the pupil. |
| 7 | Find the mean value of these points and center again. |
| 8 | Rebound the search area by going outward from this center a number of pixels equal to the radius of the last recorded ellipse. |
| 9 | Change new search area to be within picture bounds. |

Figure 9A:
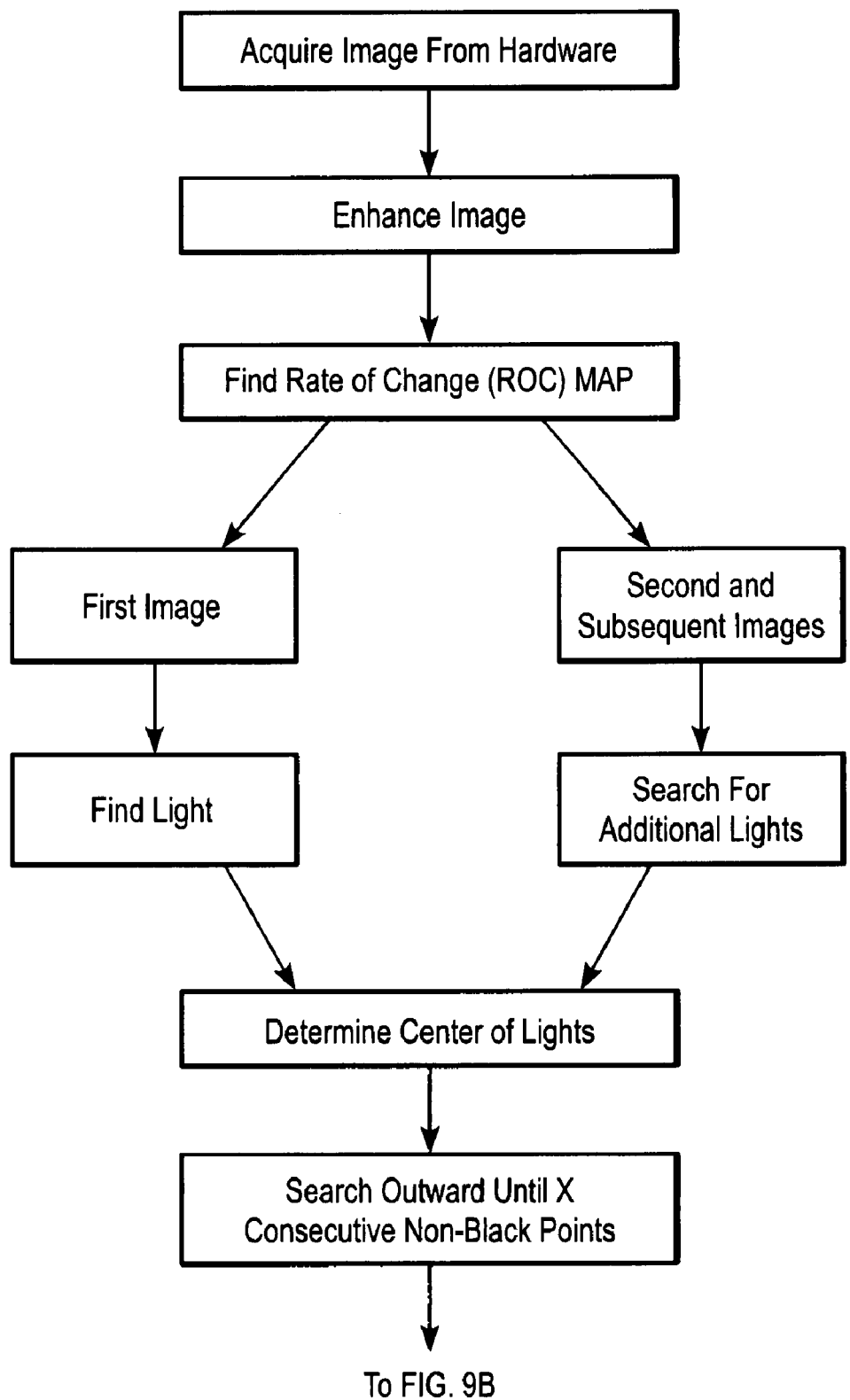
FIGS. 9a-9d are flow charts illustrating one embodiment of a method of the invention.
Figure 9B:
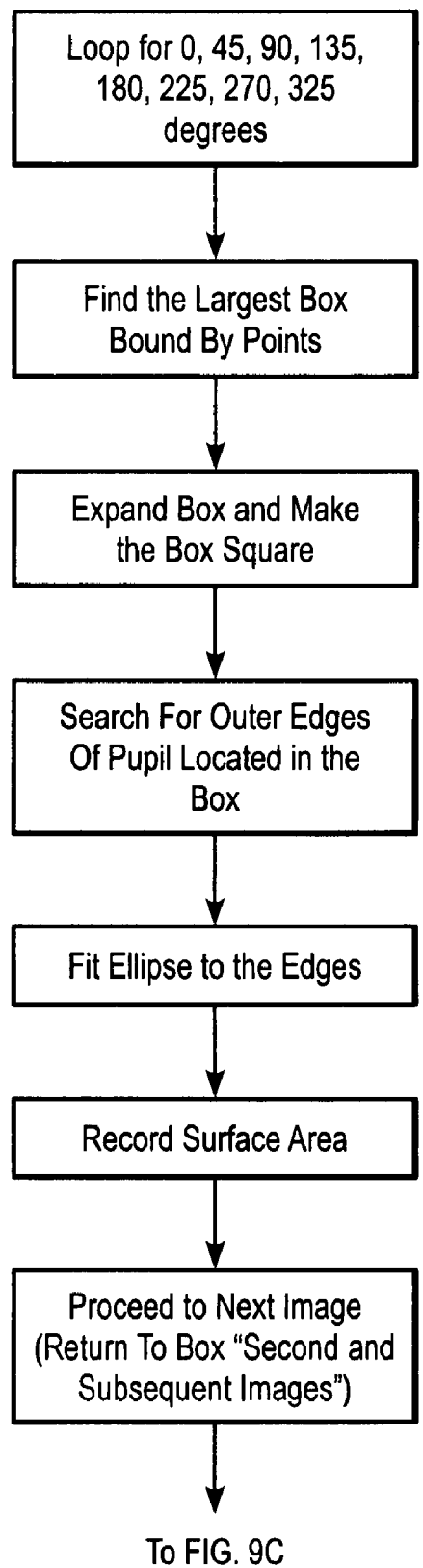
Figure 9C:
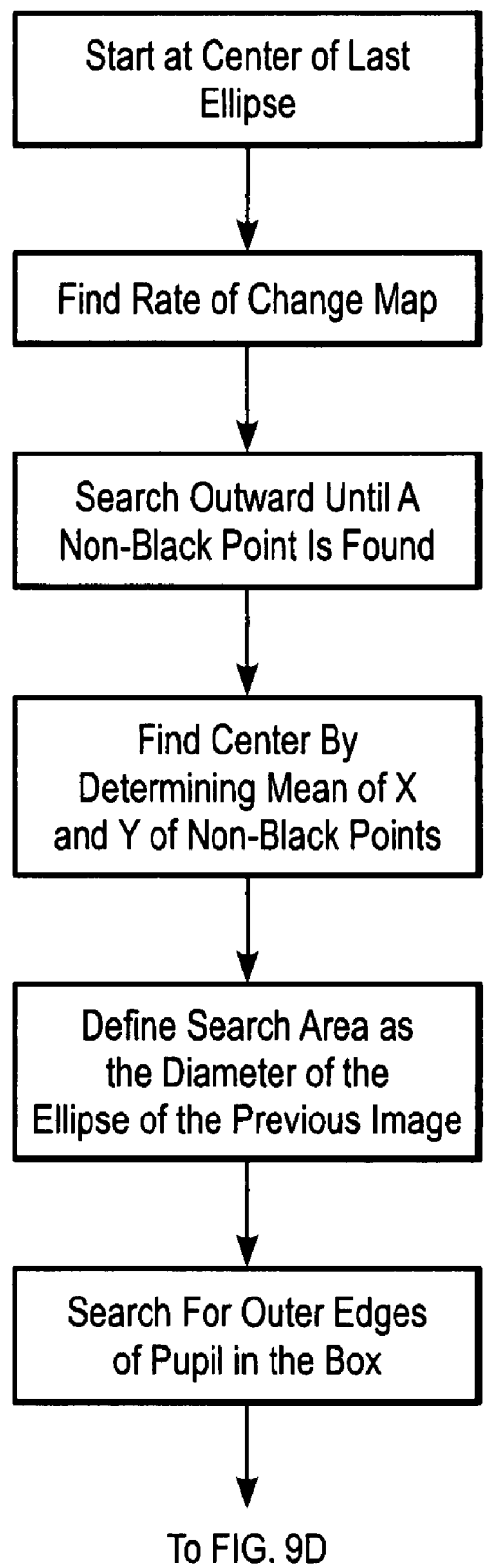
Figure 9D:
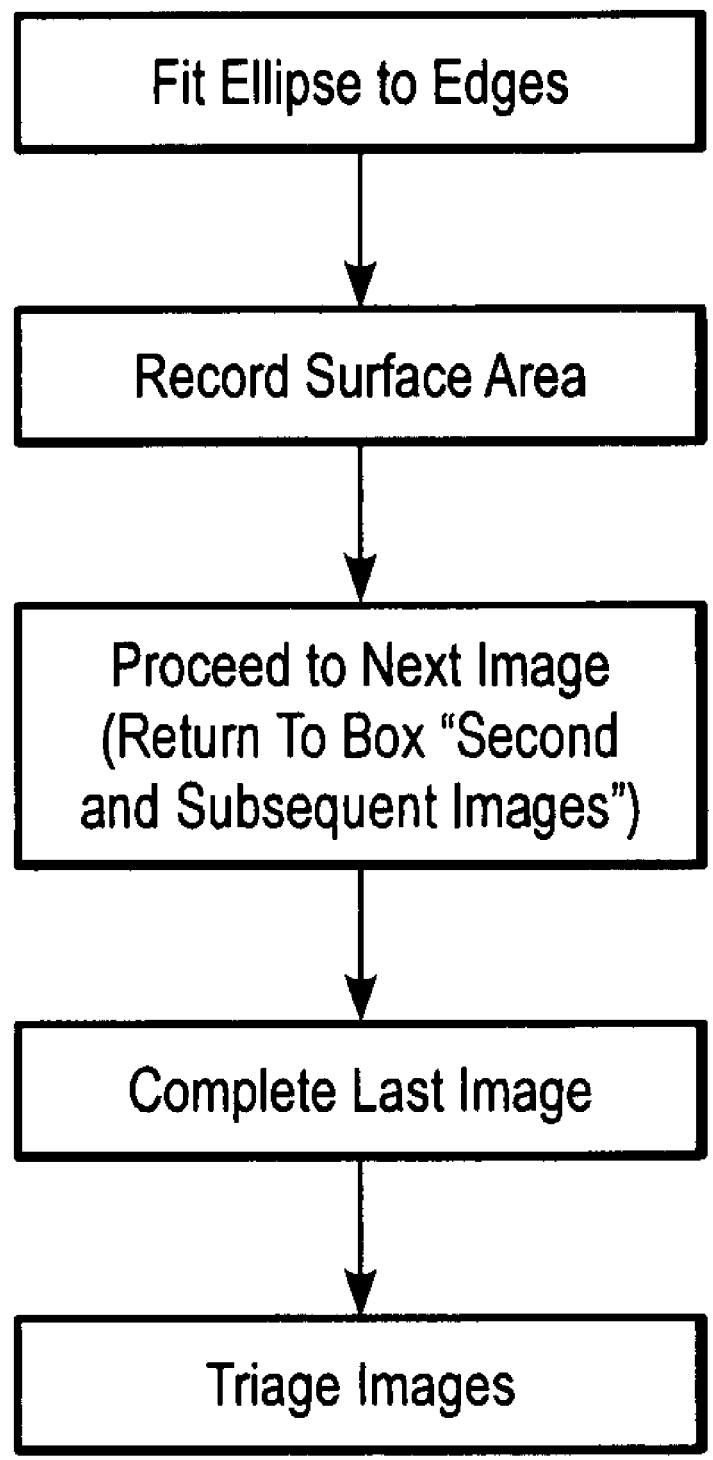
Figure 10A:
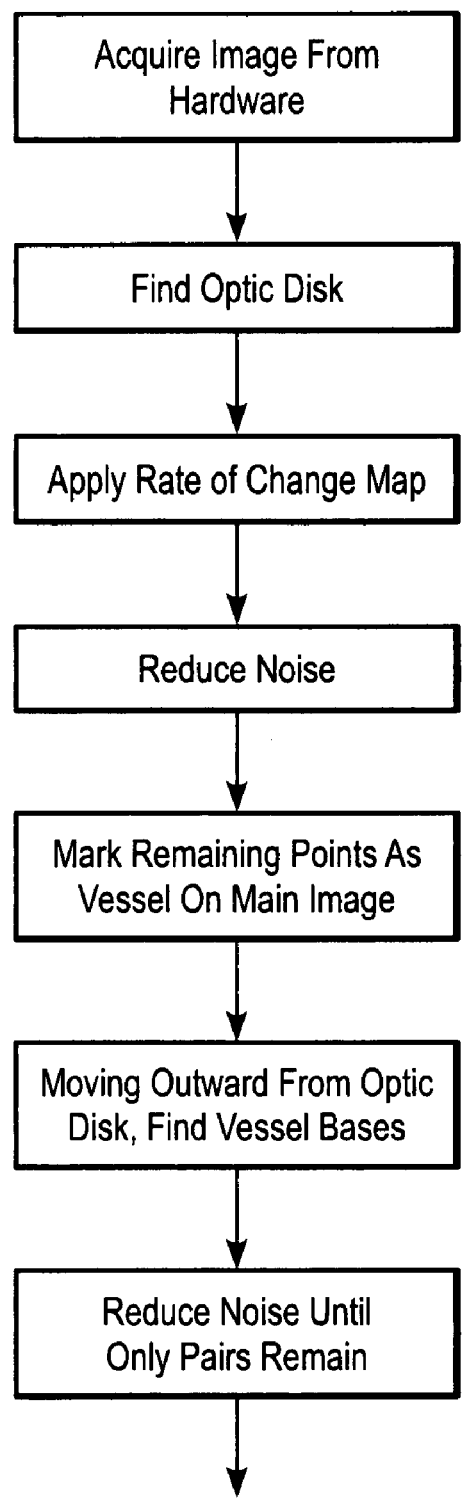
FIGS. 10a-10c are additional flow charts illustrating one embodiment of a method of the invention.
Figure 10B:
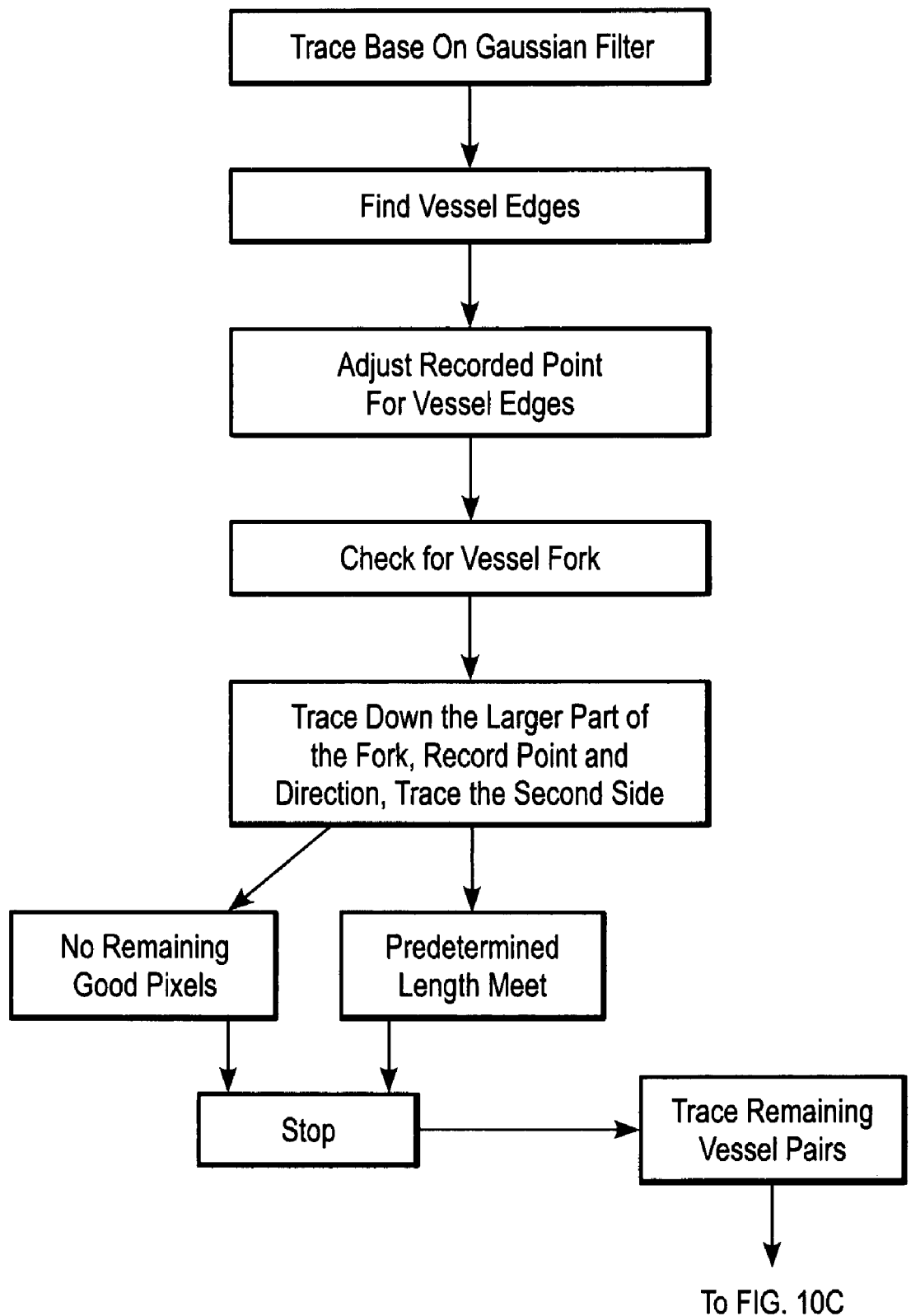
Figure 10C:
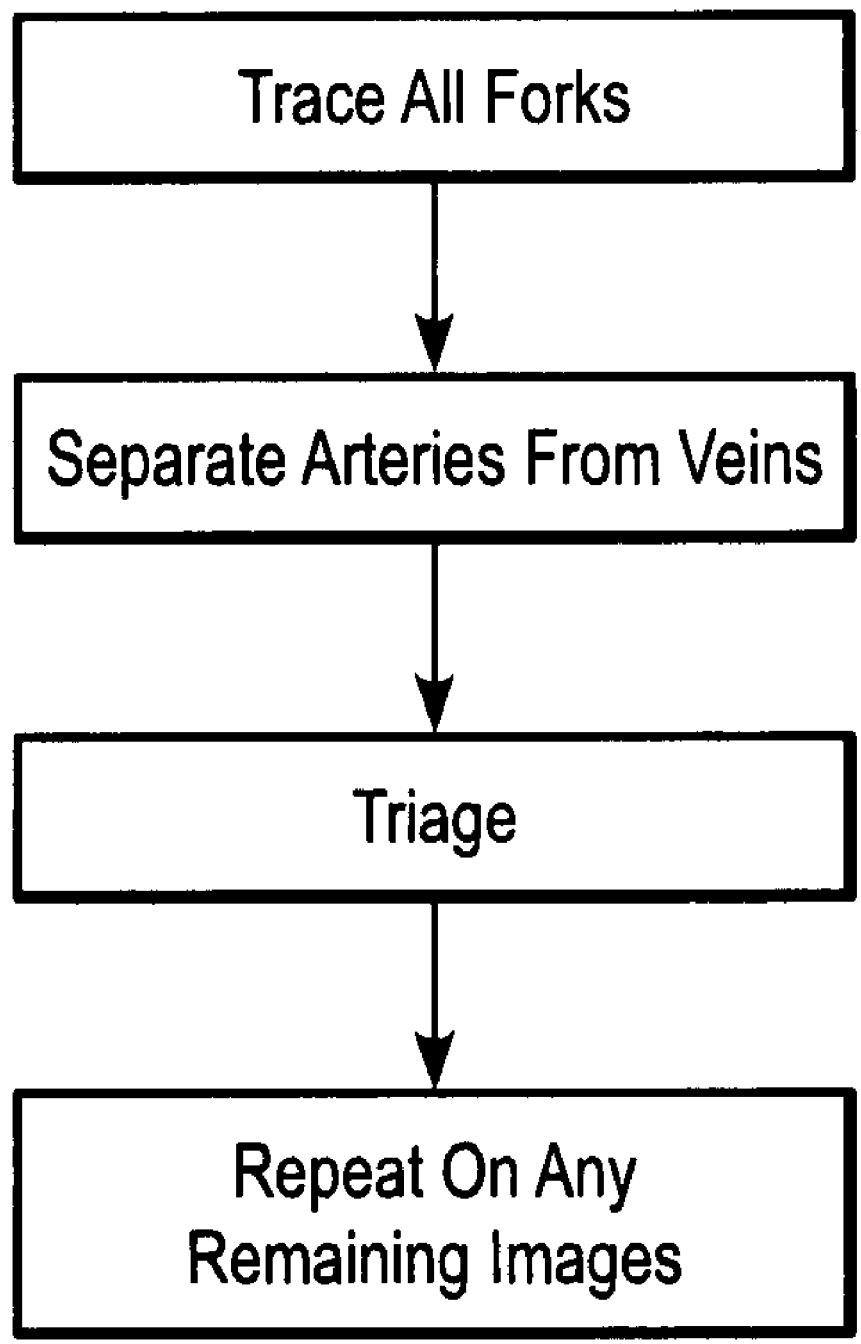

An exemplary pupil algorithm is summarized by the flow chart illustrated in FIGS. 9a through 9c.

Internal Eye Algorithms

The basic function of the internal eye (also referred here as fundus) algorithms involves locating optic vessels, determining their type (artery or vein), and then measuring the average pixel color of each type. In humans, vessels radiate out from the optic disc in all directions with distinct vessels creating a pattern which looks random (though it is not completely so). Some of the characteristics measured by the algorithm of the present invention include pupil edge detection, papillary light reflex analysis and fundal vasculature assessment. The algorithm is designed for specific feature recognition and assessment.

An example of a fundus algorithm is outlined in Table 3.

TABLE 3

Fundus Algorithm

| Step # | Direction |
|---|---|
| 1 | The pictures of the fundas are saved to a directory |
| 2 | Load each picture into a bitmap sequentially. |
| 3 | Save the green values from the bitmap into a 2D array of integers (pixels). |
| 4 | Find the average value of the matrix. |
| 5 | All of the vessels originate from the optic disk. To trace the vessels from the beginning, it is necessary to trace the optic disk. In a perfectly healthy eye, the optic disk is the brightest region in a fundus picture. Less healthy eyes have other bright spots, but the brightest pixel is usually still inside the optic disk. Therefore the optic disk is segmented out by isolating the brightest pixels. |
| 6 | Apply rate of change (ROC) map.<br>a. Fundus pictures have a near black edge around them from taking a square picture of a round viewing area, so the non-fundus section of the picture needs to be ignored.<br>b. For each pixel, take the mean differences of the current point to the 5 × 5 matrix that has the current pixel as the center, ignoring pixels that are below discard threshold.<br>c. If this ROC value is above a threshold, record it, otherwise set to 0.<br>d. This creates a map with white edges and most of the picture is black. |
| 7 | Remove low rate of change points with an average roc threshold. Given the variation in the lighting amongst the test pictures, this has to be along a gradient, varying on the ambient light level of the picture. |
| 8 | Remove pixels in low density areas (currently defined as 23 pixels or less of positive change in a given 100 pixel area). |
| 9 | Scale the points from 0 to 255 based on percentage comparison to the brightest point in the rate of change map. |
| 10 | Brighten the points by a constant to make them more visible. |
| 11 | Run a Gaussian filter over the rate of change map 3 times. |
| 12 | Determine a new threshold from the filtered image, ignore below threshold points. |
| 13 | Mark every point above a threshold (25) in the rate of change map as vessel in the main picture. |
| 14 | With all areas potentially vessel labeled, look for the bases of the vessels near the optic disk. |
| 15 | Create a search region in the 17 pixel box surrounding the box marked as optic disk. |
| 16 | Correct this search area to be in bounds. |
| 17 | Going right, down, left, and up:<br>a. Adjust the threshold based on the color value. The arteries are brighter and have less contrast with the background than the veins.<br>b. Vessels of any sort are darker than the background. Looking only at potential vessel, search for an above threshold change from light to dark. Record this point as a potential vessel base.<br>c. If a point was found in step b, search through the remaining section of potential vessel for other possible edges, based on above threshold changes in color.<br>d. If no other potential edges are found, record the last point of potential vessel as an edge. The vessel segmenting pretty well isolates the vasculature, so the end of a segment of potential vessel should either be or be within one or two pixels of the edge of a vessel.<br>e. Continue searching in the other directions. |
| 18 | Clean up the noise points from the list of potential vessel base edges. |

TABLE 3-continued

Fundus Algorithm

| Step # | Direction |
|---|---|
| 19 | Separate points into subgroups by direction. The distance from the edge of the optic disk means that any points found while going right won't be part of the base of any vessel found by going down. |
| 20 | Turn any points which are touching into one point:<br>a. If a given subset consists of only one point, drop it and search next subset.<br>b. If a given subset consists of only two points, keep the subset without filtering.<br>c. Mark the first point. If there aren't any points touching it, keep it as an edge.<br>d. If there is a point touching the first, go until the next point is more than 1 pixel away from the last recorded point.<br>e. If the touching points consist of the entire subset, keep the first and last points.<br>f. When examining the last point in a subset, compare it to the previous point instead of the next point.<br>g. If the first and last indices are still only a pixel away from each other, keep the first index. Otherwise take the middle point, rounding up when dealing with an odd number of points. |
| 21 | If there are many points close together, it is likely there is a point in the middle of a vessel. Close points should be cleared away:<br>a. Separate again into subsets by direction.<br>b. If there are only two points, keep both.<br>c. If the distance between the first and last point is less than the threshold of vessel width (8 pixels on current resolution), keep the first and last points.<br>d. Take the first 3 points. They can be either a vessel and a disconnected point, two vessels with a common edge in the middle, or the edges of a vessel with a noise point between them.<br>e. The distance between the first and second and second and third points is recorded.<br>f. If the first and second distances are less than vessel width, but together are greater, record two vessels with the middle point being recorded as a left and right edge.<br>g. If the first distance is greater than vessel width and the second distance is less, keep the second and third point.<br>h. If the second distance is greater than vessel width and the first distance is less, keep the first and second point.<br>i. If the distances together are less than vessel width, keep the first and third points. |
| 22 | Remove duplicates. |
| 23 | Merge the lists of close and far edges. |
| 24 | The vessel bases are now reduced to one pair per vessel. With the vessel bases marked, it's possible to start tracing. |
| 25 | Record the side of the picture where the optic disc is located. |
| 26 | Trace a vessel for each pair of bases. |
| 27 | Find the average color value of the points in the middle of each pair. |
| 28 | Use this average to determine the threshold for deciding whether to use the artery or vein threshold for determining the edges of the vessel. |
| 29 | Start the tracing from the point in the middle of the current pair. |
| 30 | Move all of the vessels to the left of the optic disk to the left. Move all of the vessels to the right of the optic disk to the right. Though the vessels go up and down along their path, they never go back towards the optic disk. Branches may bend back towards the disk, but the general direction of the curve doesn't change, i.e. a branch is always concave or convex in relation to the optic disk. Given this, the base's position relative to the disk causes some directions to not make since to use in searching for the next pixel of vessel. These directions are recorded in a list. |
| 31 | The directions searched for the first pixel are based on position relative to the optic disk. Viewing the optic disk as the pivot for a compass, search the pixels to the left of optic disk NW, W, SW; search pixels to the right of optic disk NE, E, SE; search pixels above the optic disk NW, N, NE; and search pixels below the optic disk SW, S, SE. |
| 32 | The search directions of later pixels are determined by the last direction of movement. If the current pixel was reached by moving North, the next pixel of vessel will be searched for in the NE, N, and NW. This is done because even in individuals with strong retinopathy the vessels make turns over the course of several pixels. |
| 33 | With the search directions determined, begin searching:<br>a. Skip search directions in the bad direction list.<br>b. Find the next point in a direction.<br>c. If that point is out of bounds, skip the current direction.<br>d. The vessels are somewhat uniform in color. Thus any large color change between the current pixel and the search pixel causes that direction to be skipped.<br>e. Run a Gaussian filter on the 5 × 5 set of pixels with the search pixel as the center. Record the Gaussian.<br>f. Of the non skipped directions, chose the direction with the lowest Gaussian value. |

TABLE 3-continued

Fundus Algorithm

| Step # | Direction |
|---|---|
| 34 | If step 33 is the end of the tracing phase, keeping the pixel in the direction of the lowest Gaussian, any vessel that doesn't cross another is completely traced. |
| 35 | Find the edges of the vessel using the point moved to, and if the point isn't the exact center of the vessel, move it to be in the center. |
| 36 | Search for the edges in directions perpendicular to the direction just moved. |
| 37 | Move one pixel in either direction and note the color differences. |
| 38 | While the distance traveled in both directions isn't greater than the vessel width and both sides haven't hit an above threshold rate of color change, move one more pixel in each direction. |
| 39 | If a large ROC value is found on one side before the other, stop moving to that side and continue searching the other side until an above threshold roc value is obtained or the maximum width is reached. |
| 40 | Movement in a direction will stop if the movement is out of bounds, or if the pixel is significantly brighter than the original pixel. The reflectance of the optic disk makes the pixels close to it brighter. |
| 41 | Pick which set of edges to keep. |
| 42 | Keep the shortest set of edges. |
| 43 | If multiple edges are the same length, keep the darkest edge. |
| 44 | If there is a tie for darkest, choose the "left" edge. |
| 45 | Record the coordinates of the kept edge. |
| 46 | The edge coordinates are adjusted to ensure they are within picture bounds. |
| 47 | If a large rate of change was hit on both edges, move the saved point to be the mid point between the two edges, rounding down. |
| 48 | If neither edge has a large rate of change, the vessel is probably forking. If the optic disk is on the left, the right fork is most likely to be the larger. If the optic disk is on the right, the left fork is most likely to be the larger. If the optic disk is on the left, keep the mid point between the mid point and the right edge. If the optic disk is on the right, keep the midpoint point between the left edge and the mid point. |
| 49 | Begin a trace in the other direction (Go back to step 32). |
| 50 | If only one side has a large rate of change, the destination point remains unchanged. |
| 51 | If the new position is in a bad direction in relation to the original point, the original point is kept. |
| 52 | If the new position is in a pixel not marked as vessel, the original point is kept. |
| 53 | If the point isn't out of bounds, the pixel is added to the list for that vessel. |
| 54 | If no valid point is found in any of the 3 directions, tracing for the current vessel is stopped. |
| 55 | Tracing otherwise stops when at 250 pixels in length. |
| 56 | Separate the vessels into arteries and veins. |
| 57 | Save the image. Arteries appear in red and veins appear in blue. |
| 58 | Record the average color values of each vessel, obtaining the values from the original picture. |
| 59 | Record the time elapsed for recording the picture. |
| 60 | Loop through the rest of the pictures in the directory. |

An exemplary fundas algorithm may be summarized by the flow chart illustrated in FIGS. 9a-9c.

Further classification may be performed on the data once the initial analysis is complete with the above algorithms. The data extracted from the ocular images taken from the patient can be compared easily to a normal eye under similar conditions, which also has been analyzed with the claimed algorithms. See FIG. 4. The norm for the ocular characteristic may be established for each subject being examined, or may be set for different population and subpopulations. A subject's quantified ocular data may then either be compared to his or her personal normal value (FIG. 5), or it can be compared to an average value established for a population to which the subject belongs (FIG. 6).

It is to be understood that the present invention is not limited to the embodiments described above, but encompasses any and all embodiments within the scope of the following claims.

What is claimed is:

1. A non-invasive device for acquiring an ocular image, comprising:
    an optic assembly comprising one or more light sources and a lens;
    an imaging system;
    a linear activator to focus the optic assembly;
    wherein the imaging system acquires an ocular image that is processed to extract one or more ocular features from the ocular image;
    wherein a rate of change map is applied, wherein the rate of change map comprises: (1) for each pixel, determining an average of the sum of the differences of the current pixel or taking a mean difference of the current pixel using a matrix that has the current pixel as the center; (2) recording this value if this value is above a threshold, otherwise setting this value to 0; and (3) creating a map with white edges and most of the picture is black;
    wherein the one or more ocular features are compared to a standard and used to identify existence of one or more ocular abnormalities, specify a type and extent of the one or more ocular abnormalities, and correlate the type and extent of the one or more ocular abnormalities to a disease state.

2. The device of claim 1, wherein the one or more light sources are LEDs, and wherein the LEDs emit light at wavelengths corresponding to near infrared light.

3. The device of claim 1, wherein the one or more light sources are LEDs, and wherein the LEDs emit light at wavelengths corresponding to visible light.

4. The device of claim 1, wherein the diseased state is selected from the group consisting of: exposure to organophosphate nerve agents, exposure to cyanide compounds, exposure to carbon monoxide, exposure to botulinum toxin, and combinations thereof.

5. The device of claim 1, wherein the processing of the ocular image is performed on the device.

6. The device of claim 1, wherein the one or more ocular abnormalities are classified.

7. The device of claim 1, wherein the one or more light sources are light emitting diodes.

8. A non-invasive method of diagnosing a disease state, the method comprising:
   accessing an ocular image;
   applying a rate of change map, wherein the rate of change map comprises: (1) for each pixel, determining an average of the sum of the differences of the current pixel or taking a mean difference of the current pixel using a matrix that has the current pixel as the center; (2) recording this value if this value is above a threshold, otherwise setting this value to 0; and (3) creating a map with white edges and most of the picture is black;
   processing the ocular image to extract ocular characteristics;
   classifying the ocular characteristics to determine one or more ocular abnormalities or ocular damage;
   comparing the one or more ocular abnormalities to a standard; and
   determining whether the ocular characteristics are abnormal, a type of disease state, and severity of the disease state.

9. The method of claim 8, further comprising acquiring the ocular image using a non-invasive device comprising an optic assembly comprising one or more light sources and a lens, an imaging system, and a linear activator to focus the optic assembly.

10. The method of claim 9, wherein the one or more light sources are light emitting diodes.

11. The method of claim 8, further comprising comparing the ocular image to standard images in a collected database for determining whether the ocular characteristics are abnormal.

12. The method of claim 8, further comprising comparing the ocular image to previous ocular images for the same subject in a collected database for determining a progression of the one or more ocular abnormalities or ocular damage.

13. The method of claim 8, further comprising determining pupil size based upon an average color measurement of the ocular image.

14. The method of claim 13, wherein the determining pupil size comprises making points above an average color threshold white, fitting dark areas of the ocular image with an approximated ellipse, and using an x- and y-radii of the approximated ellipse to calculate pupil surface area.

15. The method of claim 8, further comprising determining pupil size by determining a center of lights, searching outwardly until a set number of consecutive non-black points are found, superimposing a box, searching for outer edges of a pupil located in the box, fitting an ellipse to edges of the box, and recording surface area.

16. The method of claim 15, further comprising repeating the determining of pupil size for a second pupil of a subject.

17. The method of claim 8, further comprising locating one or more optic vessels, determining type of the one or more optic vessels, and measuring average pixel color of each of the one or more optic vessels.

18. The method of claim 17, further comprising one or more of pupil edge detection, pupillary light reflex analysis, and fundal vascular assessment.

19. The method of claim 17, further comprising finding an optic disk in the ocular image, finding vessel bases, finding vessel edges, and checking for vessel forks.

20. The method of claim 19, further comprising tracing down a larger part of a vessel fork, if present, for a predetermined length.

21. The method of claim 20, further comprising repeating the tracing for other vessel forks in the ocular image.

22. The method of claim 8, further comprising determining pupil size based upon low intensity light, determining pupil size based upon high intensity light, determining venous coloration, determining arterial coloration, and determining strobe light cutoff frequency.

23. The method of claim 8, further comprising enhancing the ocular image prior to processing the ocular image.

24. The method of claim 8, wherein the disease states are selected from the group consisting of: exposure to organophosphate nerve agents, exposure to cyanide compounds, exposure to carbon monoxide, exposure to botulinum toxin, and combinations thereof.

25. The method of claim 8, wherein the standard is an average normal value established for a population.

26. The method of claim 8, further comprising finding lights in the ocular image, determining a center of the lights, searching outwardly until a predetermined number of consecutive points are non-black, finding a largest box bound by points, search for outer edges of pupil located in the box, fitting an ellipse to the edges, and recording a surface area.

27. The method of claim 26, further comprising finding additional lights in a second ocular image, determining a center of the additional lights, searching outwardly until a non-black point is found, finding a center by determining a mean of x and y of non-black points, defining a search area as a diameter of the ellipse of the first ocular image, searching for an outer edge of pupil in the box, fitting an ellipse to the edge, and recording a surface area.

* * * * *